United States Patent [19]

O'Dowd

[11] Patent Number: 5,591,602
[45] Date of Patent: Jan. 7, 1997

[54] NUCLEIC ACID ENCODING OPIOID RECEPTOR

[76] Inventor: Brian F. O'Dowd, 229 Catalina Drive, Scarborough, Ontario, Canada

[21] Appl. No.: 148,215

[22] Filed: Nov. 5, 1993

[51] Int. Cl.$^6$ .................. C12N 15/12; C07K 14/705; C07H 21/00
[52] U.S. Cl. .................. 435/69.1; 536/23.5; 536/24.31; 435/240.2; 435/252.3; 435/254.11; 435/320.1
[58] Field of Search .................. 435/69.1, 240.1, 435/320.1, 252.3, 254.11, 240.2; 536/23.1, 23.5, 24.31

[56] References Cited

FOREIGN PATENT DOCUMENTS

WO94/11500  5/1994  WIPO.

OTHER PUBLICATIONS

Giordano et al., "Antagonist–Induced Up–Regulation of the Putative Epsilon Opioid Receptor in Rat Brain: Comparison with Kappa, Mu and Delta Opioid Receptors," *The Journal of Pharmacology and Experimental Therapeutics*, 255(2):536–540, 1990.
Nock et al., "Properties of the Putative Epsilon Opioid Receptor: Identification in Rat, Guinea Pig, Cow, Pig and Chicken Brain," *The Journal of Pharmacology and Experimental Therapeutics*, 264(1): 349–359, 1993.
Libert et al., Science, vol. 244, p. 569, 1989.
Garzon et al., Mol. Pharmacology, 28, pp. 1–9, 1985 (Abstract).
Chen et al., Mol. Pharmacology, 44, pp. 8–12, 1993.
Evans et al., Soc. for Neurosci, 18, p. 16.1, 1992.
Dohlman et al., "Model Systems for the Study of Seven–Transmembrane–Segment Receptors," *Annu. Rev. Biochem.*, 60:653–688, 1991.
Dohlman et al., "A Family of Receptors Coupled to Guanine Nucleotide Regulatory Proteins," *Biochemistry*, 26:2657–2664, 1987.
Evans et al., "Cloning of Delta Opioid Receptor by Functional Expression," *Science*, 258:1952–1954, 1992.
Frielle et al., "Structural Basis of β–adrenergic Receptor Subtype Specificity Studied with Chimeric β1/β2–adrenergic Receptors," *Proc. Natl. Acad. Sci. USA*, 85:9494–9498, 1988.
Gioannini, T. L. et al., "Evidence for the Presence of Disulfide Bridges in Opioid Receptors Essential for Ligand Binding. Possible Role in Receptor Activation," *J. Mol. Recogn.*, 2:44–48, 1989.
Kieffer et al., "The δ–opioid Receptor: Isolation of a cDNA by Expression Cloning and Pharmacological Characterization," *Proc. Natl. Acad. Sci. USA*, 89:12048–12052, 1992.
Loh et al., "Molecular Characterization of Opioid Receptors," *Annu. Rev. Pharmacol. Toxicol.*, 30:123–147, 1990.
Lutz et al., "Opioid Receptors and Their Phamacological Profiles," *J. Receptor Res.*, 12:267–286, 1992.
Mansour et al., "Anatomy of CNS Opioid Receptors," *Trends in Neurosci.*, 7:2445–2453, 1987.
Nock et al., "Autoradiography of [3H]U–69593 Binding Sites in Rat Brain: Evidence for K Opioid Receptor Subtypes," *Eur. J. Pharmacol.*, 154:27–34, 1988.
Simon, "Opioid Receptors and Endogenous Opioid Peptides," *Medicinal Res. Rev.*, 11:357–374, 1991.
Unterwald et al., "Neuroanatomical Localization of K1 and K2 Opioid Receptors in Rat and Guinea Pig Brain," *Brain Res.*, 562:57–65, 1991.
Xie et al., "Expression Cloning of cDNA Encoding a Seven–helix Receptor from Human Placenta with Affinity for Opioid Ligands," *Proc. Natl. Acad. Sci. USA*, 89:4124–4128, 1992.
Yamada et al., "Cloning and Functional Characterization of a Family of Human and Mouse Somatostatin Receptors Expressed in Brain, Gastrointestinal Tract, and Kidney," *Proc. Natl. Acad. Sci. USA*, 89:251–255, 1992.
Yasuda et al., "Cloning of a Novel Somatostatin Receptor, SSTR3, Coupled to Adenylylcyclase," *J. Biol. Chem.*, 267:20422–20428, 1992.
Schofield et al., "Molecular Characterization of a New Immunoglobulin Superfamily Protein with Potential Roles in Opioid Binding and Cell Contact," *The EMBO Journal*, 8:489–495, 1989.
Probst et al., "Sequence Alignment of the G–Protein Coupled Receptor Superfamily," *DNA and Cell Biology*, 11:1–20, 1992.
Dialog Search Report, pp. 1–14, printed May 24, 1994.

*Primary Examiner*—Stephen G. Walsh
*Assistant Examiner*—Sally P. Teng
*Attorney, Agent, or Firm*—Arnold, White & Durkee

[57] ABSTRACT

The invention relates generally to compositions of and methods for obtaining epsilon opioid receptor polypeptides. The invention relates as well to polynucleotides encoding epsilon opioid receptor polypeptides, the recombinant vectors carrying those sequences, the recombinant host cells including either the sequences or vectors, and recombinant opioid receptor polypeptides. The invention includes as well, methods for using the isolated, recombinant receptor polypeptide in assays designed to select and improve substances capable of interacting with epsilon opioid receptor polypeptides for use in diagnostic, drug design and therapeutic applications.

14 Claims, 12 Drawing Sheets

FIG. 1A

```
ACCTATGCTT TAAATTCCTC TTTCCCTTGG GGGACGCCAG GTCGCCGGCT CCTCTGCCCT    60

CGTTGAG ATG GAC AAC GCC TCG GAG CCC TTC TCG GAG CCC TTC TCG GAG CCC TGG CCC GCC AAC GCA   109
        Met Asp Asn Ala Ser Phe Ser Glu Pro Trp Pro Ala Asn Ala
        1                5                              10

TCG GGC CCG GAC CCG GCG CTG AGC TGC TCC AAC GCG TCG ACT CTG GCG   157
Ser Gly Pro Asp Pro Ala Leu Ser Cys Ser Asn Ala Ser Thr Leu Ala
15                  20                  25                  30

CCG CCG GCG CCG CTG CCG CTG GCT GTA CCA GTT GTC TAC GCG GTG   205
Pro Leu Pro Ala Pro Leu Ala Val Ala Val Pro Val Val Tyr Ala Val
35                  40                  45

ATC TGC GCC GTG GGT CTG GCC AAC TCC GCC GTG TAC GTG TTG   253
Ile Cys Ala Val Gly Leu Ala Gly Asn Ser Ala Val Leu Tyr Val Leu
50                  55                  60

CTG CGG GCG CCC CGC ATG AAG ACC GTC ACC AAC CTG TTC ATC CTC AAC   301
Leu Arg Ala Pro Arg Met Lys Thr Val Thr Asn Leu Phe Ile Leu Asn
65                  70                  75

CTG GCC ATC GCC GAC GAG CTC TTC ACG CTG GTG CTG CCC ATC AAC ATC   349
Leu Ala Ile Ala Asp Glu Leu Phe Thr Leu Val Leu Pro Ile Asn Ile
80                  85                  90

GCC GAC TTC CTG CTG CGG CAG TGG CCC TTC GGG GAG CTC ATG TGC AAG   397
Ala Asp Phe Leu Leu Arg Gln Trp Pro Phe Gly Glu Leu Met Cys Lys
95                  100                 105                 110
```

```
CTC ATC GTG GCT ATC GAC CAG TAC AAC ACC TTC TCC AGC CTC TAC TTC    445
Leu Ile Val Ala Ile Asp Gln Tyr Asn Thr Phe Ser Ser Leu Tyr Phe
            115                 120                 125

CTC ACC GTC ATG AGC GCC GAC CGC TAC CTG GTG GTG TTG GCC ACT GCG    493
Leu Thr Val Met Ser Ala Asp Arg Tyr Leu Val Val Leu Ala Thr Ala
            130                 135                 140

GAG TCG CGC CGG GTG GCC CGC GGC CGC GCG GCC GCG CGC GCG GTG        541
Glu Ser Arg Arg Val Ala Gly Ala Arg Thr Ser Ala Ala Arg Ala Val
        145                 150                 155

AGC CTG GCC GTG TGG GGG ATC GTC ACA CTC GTC CTG CCC TTC GCA        589
Ser Leu Ala Val Trp Gly Ile Val Thr Leu Val Leu Pro Phe Ala
160                 165                 170

GTC GCC CGG CTA GAC GAC GAG CAG GGC CGG CGC CAG TGC GTG CTA        637
Val Phe Ala Arg Leu Asp Asp Glu Gln Gly Arg Arg Gln Cys Val Leu
175                 180                 185                 190

GTC TTT CCG CAG CCC GAG GCC TTC TGG TGG CGC GCG AGC CGC CTC TAC    685
Val Phe Pro Gln Pro Glu Ala Phe Trp Trp Arg Ala Ser Arg Leu Tyr
195                 200                 205

ACG CTC GTG CTG GGC TTC GCC ATC CCC GTG TCC ACC ATC TGT GTC CTC    733
Thr Leu Val Leu Gly Phe Ala Ile Pro Val Ser Thr Ile Cys Val Leu
            210                 215                 220
```

FIG.1B

```
TAT ACC ACC CTG CTG TGC CGG CTG CAT GCC ATG CGG CTG GAC AGC CAC    781
Tyr Thr Thr Leu Leu Cys Arg Leu His Ala Met Arg Leu Asp Ser His
225                         230                         235

GCC AAG GCC CTG GAG CGC GCC AAG AAG CGG GTG ACC TTC CTG GTG GTG    829
Ala Lys Ala Leu Glu Arg Ala Lys Lys Arg Val Thr Phe Leu Val Val
240                         245                         250

GCA ATC CTG GCG GTG TGC GCC CTC CTC TGC TGG ACG CCC TAC CAC CTG AGC    877
Ala Ile Leu Ala Val Cys Ala Leu Leu Cys Trp Thr Pro Tyr His Leu Ser
255                         260                         265                         270

ACC GTG GCG CTC ACC GAC CTC CCG CAG ACG CCG CTG GTC ATC    925
Thr Val Ala Leu Thr Asp Leu Pro Gln Thr Pro Leu Val Ile
275                         280                         285

GCT ATC TCC TAC TTC ATC ACC AGC CTG TAC GCC AAC AGC TGC CTC    973
Ala Ile Ser Tyr Phe Ile Thr Ser Leu Tyr Ala Asn Ser Cys Leu
290                         295                         300

AAC CCC TTC CTC TAC GCC TTC CTG GAC GCC TTC AGC TTC CGC AGG AAC CTC    1021
Asn Pro Phe Leu Tyr Ala Phe Leu Asp Ala Phe Ser Phe Arg Arg Asn Leu
305                         310                         315

CGC CAG CTG ATA ACT TGC CGC GCG GCA GCC TGA    1054
Arg Gln Leu Ile Thr Cys Arg Ala Ala Ala
320                         325
```

FIG.1C

```
TCCACTAGTA ACGGCCGCCA GGATCCACAT CTCTTCCCAG GAGGGTGGCC AGCAGCTGCT        60
CTCTGCGGGA GGAGGAACT GATCTGCTGA AGTCTCACCA GGAAGAGGCG GGAAGGCCCC       120
CACACACCCC ACCAGGCTCC CTCTGGCCCC ATGTCCTTGA CCTGGCAAAG TGGCCGCAGT       180
CTCTGCCAGA GAACCTGGAG TGGCTGTGCC TAACAGACGG CTGGATCTCA AAGTCTCTGG       240
TTGTTTTCT TTCCTAGAAT CCAGCCTAAG GAGGCCCCCA ACCAGATACC CAACTCCAAG       300
GCACCTCCCA CCTGCCCAGG GCGCAAATCG TCAACGGTCC CAGCTACA ATG CAG GCC       357
                                                    Met Gln Ala
                                                      1

GCT GGG CAC CCA GAG CCC CTT GAC AGC AGG GGC TCC TTC TCC CCC            405
Ala Gly His Pro Glu Pro Leu Asp Ser Arg Gly Ser Phe Ser Pro
  5                          10                     15

ACG ATG GGT GCC AAC GTC TCT CAG GAC AAT GGC ACT GGC CAC AAT GCC        453
Thr Met Gly Ala Asn Val Ser Gln Asp Asn Gly Thr Gly His Asn Ala
 20                      25                      30              35

ACC TTC TCC GAG CCA CTG CCG TTC CTC TAT GTG GTG CTC CCC GCC GTG        501
Thr Phe Ser Glu Pro Leu Pro Phe Leu Tyr Val Val Leu Pro Ala Val
         40                      45                      50

TAC TCC GGG ATC TGT GCT GTG GGG CTG ACT GGC AAC ACG GCC GTC ATC        549
Tyr Ser Gly Ile Cys Ala Val Gly Leu Thr Gly Asn Thr Ala Val Ile
 55                      60                      65
```

FIG. 2A

```
CTT GTA ATC CTA AGG GCG CCC AAG ATG AAG ACG GTG ACC AAC GTG TTC    597
Leu Val Ile Leu Arg Ala Pro Lys Met Lys Thr Val Thr Asn Val Phe
             70                  75                  80

ATC CTG AAC CTG GCC GTC GCC GAC GGG CTC TTC ACG CTG GTA CTG CCC    645
Ile Leu Asn Leu Ala Val Ala Asp Gly Leu Phe Thr Leu Val Leu Pro
             85                  90                  95

GTC AAC ATC GCG GAG CAC CTG CTG CAG TAC TGG CCC TTC GGG GAG CTG    693
Val Asn Ile Ala Glu His Leu Leu Gln Tyr Trp Pro Phe Gly Glu Leu
            100                 105                 110                 115

CTC TGC AAG CTG GTG CTG AGC GTC GAC CAC TAC AAC ATC TTC TCC AGC    741
Leu Cys Lys Leu Val Leu Ser Val Asp His Tyr Asn Ile Phe Ser Ser
            120                 125                 130

ATC TAC TTC CTA ACC GCC GTG ATG AGC GTC GAC CGA TAC CTG GTG CTG    789
Ile Tyr Phe Leu Thr Ala Val Met Ser Val Asp Arg Tyr Leu Val Leu
            135                 140                 145

GCC ACC GTG AGG TCC CGC CAC ATG CCC TGG CGC ACC TAC CGG GGG GCG    837
Ala Thr Val Arg Ser Arg His Met Pro Trp Arg Thr Tyr Arg Gly Ala
            150                 155                 160

AAG GTC GCC AGC CTG TGT GTC TGG CTG GGC GTC ACG GTC CTG GTT CTG    885
Lys Val Ala Ser Leu Cys Val Trp Leu Gly Val Thr Val Leu Val Leu
            165                 170                 175
```

FIG. 2B

```
CCC TTC TTC TCT TTC GCT GGC GTC TAC AGC AAC GAG CTG CAG GTC CCA    933
Pro Phe Phe Ser Phe Ala Gly Val Tyr Ser Asn Glu Leu Gln Val Pro
180                     185                 190                 195

AGC TGT GGG CTG AGC TTC CCG TGG CCC GAG GTC TGG TTC AAG GCC        981
Ser Cys Gly Leu Ser Phe Pro Trp Pro Glu Val Trp Phe Lys Ala
    200                 205                 210

AGC CGT GTC TAC ACT TTG GTC CTG GGC TTC GTG CTG CCC GTG TGC ACC   1029
Ser Arg Val Tyr Thr Leu Val Leu Gly Phe Val Leu Pro Val Cys Thr
215                 220                 225

ATC TGT GTG CTC TAC ACA GAC CTC TGG CTG CGC AGG CTG CGG GTG CGG   1077
Ile Cys Val Leu Tyr Thr Asp Leu Trp Leu Arg Arg Leu Arg Val Arg
            230                 235                 240

CTC CGC TCT GGA GCC AAG GCT CTA GGC AAG GCC AGG CGG AAG GTG ACC   1125
Leu Arg Ser Gly Ala Lys Ala Leu Gly Lys Ala Arg Arg Lys Val Thr
        245                 250                 255

GTC CTC GTC CTC GTG GCC GTG CTC TGC TGG ACG CCC   1173
Val Leu Val Leu Val Leu Ala Val Leu Cys Leu Cys Trp Thr Pro
260                 265                 270                 275

TTC CAC CTG GCC TCT GTG GTG GCC CTG ACC ACG GAC CTG CCC CAG ACC   1221
Phe His Leu Ala Ser Val Val Ala Leu Thr Thr Asp Leu Pro Gln Thr
            280                 285                 290
```

FIG.2C

```
CCA CTG GTC ATC AGT ATG TCC TAC GTC ATC ACC AGC CTC ACG TAC GCC    1269
Pro Leu Val Ile Ser Met Ser Tyr Val Ile Thr Ser Leu Thr Tyr Ala
                295                 300                 305

AAC TCG TGC CTG AAC CCC TTC CTC TAC GCC TTT CTA GAT GAC AAC TTC    1317
Asn Ser Cys Leu Asn Pro Phe Leu Tyr Ala Phe Leu Asp Asp Asn Phe
                310                 315                 320

CGG AAG AAC TTC CGC AGC ATA TTG CGG TGC TGA AGGGCCT GGGCACCATC     1367
Arg Lys Asn Phe Arg Ser Ile Leu Arg Cys
                325                 330

ATCCCCATCA TCATCATCAC CCCCATCATC ATCACCCCCA CCATTACCCC CATCGTCACG   1427

CCCATCATCA CGCCCATCAT CACCCCCCAT CATCACCCCC ATCATCATGC CCATCATCAC   1487

CCCCCATCAT CATCATGCCC ACCCCTCATC A                                 1518
```

FIG.2D

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 1054 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 68..1051

( x i ) SEQUENCE DESCRIPTION: SEQ ID NO:1:

```
ACCTATGCTT TAAATTCCTC TTTCCCTTGG GGGACGCCAG GTCGCCGGCT CCTCTGCCCT        60

CGTTGAG ATG GAC AAC GCC TCG TTC TCG GAG CCC TGG CCC GCC AAC GCA        109
        Met Asp Asn Ala Ser Phe Ser Glu Pro Trp Pro Ala Asn Ala
```

|   | 1 | | | | 5 | | | | | 10 | | | | | |
|---|---|---|---|---|---|---|---|---|---|---|---|---|---|---|---|
| TCG | GGC | CCG | GAC | CCG | GCG | CTG | AGC | TGC | TCC | AAC | GCG | TCG | ACT | CTG | GCG | 157 |
| Ser | Gly | Pro | Asp | Pro | Ala | Leu | Ser | Cys | Ser | Asn | Ala | Ser | Thr | Leu | Ala |
| 15 | | | | | 20 | | | | | 25 | | | | | 30 |
| CCG | CTG | CCG | GCG | CCG | CTG | GCG | GTG | GCT | GTA | CCA | GTT | GTC | TAC | GCG | GTG | 205 |
| Pro | Leu | Pro | Ala | Pro | Leu | Ala | Val | Ala | Val | Pro | Val | Val | Tyr | Ala | Val |
| | | | | 35 | | | | 40 | | | | | 45 | | |
| ATC | TGC | GCC | GTG | GGT | CTG | GCG | GGC | AAC | TCC | GCC | GTG | CTG | TAC | GTG | TTG | 253 |
| Ile | Cys | Ala | Val | Gly | Leu | Ala | Gly | Asn | Ser | Ala | Val | Leu | Tyr | Val | Leu |
| | | | 50 | | | | | 55 | | | | | 60 | | |
| CTG | CGG | GCG | CCC | CGC | ATG | AAG | ACC | GTC | ACC | AAC | CTG | TTC | ATC | CTC | AAC | 301 |
| Leu | Arg | Ala | Pro | Arg | Met | Lys | Thr | Val | Thr | Asn | Leu | Phe | Ile | Leu | Asn |
| | | 65 | | | | 70 | | | | | 75 | | | | |
| CTG | GCC | ATC | GCC | GAC | GAG | CTC | TTC | ACG | CTG | GTG | CTG | CCC | ATC | AAC | ATC | 349 |
| Leu | Ala | Ile | Ala | Asp | Glu | Leu | Phe | Thr | Leu | Val | Leu | Pro | Ile | Asn | Ile |
| | 80 | | | | | 85 | | | | | 90 | | | | |
| GCC | GAC | TTC | CTG | CTG | CGG | CAG | TGG | CCC | TTC | GGG | GAG | CTC | ATG | TGC | AAG | 397 |
| Ala | Asp | Phe | Leu | Leu | Arg | Gln | Trp | Pro | Phe | Gly | Glu | Leu | Met | Cys | Lys |
| 95 | | | | | 100 | | | | | 105 | | | | | 110 |
| CTC | ATC | GTG | GCT | ATC | GAC | CAG | TAC | AAC | ACC | TTC | TCC | AGC | CTC | TAC | TTC | 445 |
| Leu | Ile | Val | Ala | Ile | Asp | Gln | Tyr | Asn | Thr | Phe | Ser | Ser | Leu | Tyr | Phe |
| | | | | 115 | | | | 120 | | | | | 125 | | |
| CTC | ACC | GTC | ATG | AGC | GCC | GAC | CGC | TAC | CTG | GTG | GTG | TTG | GCC | ACT | GCG | 493 |
| Leu | Thr | Val | Met | Ser | Ala | Asp | Arg | Tyr | Leu | Val | Val | Leu | Ala | Thr | Ala |
| | | | 130 | | | | | 135 | | | | | 140 | | |
| GAG | TCG | CGC | CGG | GTG | GCC | GGC | CGC | ACC | TAC | AGC | GCC | GCG | CGC | GCG | GTG | 541 |
| Glu | Ser | Arg | Arg | Val | Ala | Gly | Arg | Thr | Tyr | Ser | Ala | Ala | Arg | Ala | Val |
| | | 145 | | | | | 150 | | | | | 155 | | | |
| AGC | CTG | GCC | GTG | TGG | GGG | ATC | GTC | ACA | CTC | GTC | GTG | CTG | CCC | TTC | GCA | 589 |
| Ser | Leu | Ala | Val | Trp | Gly | Ile | Val | Thr | Leu | Val | Val | Leu | Pro | Phe | Ala |
| | 160 | | | | | 165 | | | | | 170 | | | | |
| GTC | TTC | GCC | CGG | CTA | GAC | GAC | GAG | CAG | GGC | CGG | CGC | CAG | TGC | GTG | CTA | 637 |
| Val | Phe | Ala | Arg | Leu | Asp | Asp | Glu | Gln | Gly | Arg | Arg | Gln | Cys | Val | Leu |
| 175 | | | | | 180 | | | | | 185 | | | | | 190 |
| GTC | TTT | CCG | CAG | CCC | GAG | GCC | TTC | TGG | TGG | CGC | GCG | AGC | CGC | CTC | TAC | 685 |
| Val | Phe | Pro | Gln | Pro | Glu | Ala | Phe | Trp | Trp | Arg | Ala | Ser | Arg | Leu | Tyr |
| | | | | 195 | | | | 200 | | | | | 205 | | |
| ACG | CTC | GTG | CTG | GGC | TTC | GCC | ATC | CCC | GTG | TCC | ACC | ATC | TGT | GTC | CTC | 733 |
| Thr | Leu | Val | Leu | Gly | Phe | Ala | Ile | Pro | Val | Ser | Thr | Ile | Cys | Val | Leu |
| | | | 210 | | | | | 215 | | | | | 220 | | |
| TAT | ACC | ACC | CTG | CTG | TGC | CGG | CTG | CAT | GCC | ATG | CGG | CTG | GAC | AGC | CAC | 781 |
| Tyr | Thr | Thr | Leu | Leu | Cys | Arg | Leu | His | Ala | Met | Arg | Leu | Asp | Ser | His |
| | | 225 | | | | | 230 | | | | | 235 | | | |
| GCC | AAG | GCC | CTG | GAG | CGC | GCC | AAG | AAG | CGG | GTG | ACC | TTC | CTG | GTG | GTG | 829 |
| Ala | Lys | Ala | Leu | Glu | Arg | Ala | Lys | Lys | Arg | Val | Thr | Phe | Leu | Val | Val |
| | 240 | | | | | 245 | | | | | 250 | | | | |
| GCA | ATC | CTG | GCG | GTG | TGC | CTC | CTC | TGC | TGG | ACG | CCC | TAC | CAC | CTG | AGC | 877 |
| Ala | Ile | Leu | Ala | Val | Cys | Leu | Leu | Cys | Trp | Thr | Pro | Tyr | His | Leu | Ser |
| 255 | | | | | 260 | | | | | 265 | | | | | 270 |
| ACC | GTG | GTG | GCG | CTC | ACC | ACC | GAC | CTC | CCG | CAG | ACG | CCG | CTG | GTC | ATC | 925 |
| Thr | Val | Val | Ala | Leu | Thr | Thr | Asp | Leu | Pro | Gln | Thr | Pro | Leu | Val | Ile |
| | | | | 275 | | | | 280 | | | | | 285 | | |
| GCT | ATC | TCC | TAC | TTC | ATC | ACC | AGC | CTG | ACG | TAC | GCC | AAC | AGC | TGC | CTC | 973 |
| Ala | Ile | Ser | Tyr | Phe | Ile | Thr | Ser | Leu | Thr | Tyr | Ala | Asn | Ser | Cys | Leu |
| | | | 290 | | | | | 295 | | | | | 300 | | |
| AAC | CCC | TTC | CTC | TAC | GCC | TTC | CTG | GAC | GCC | AGC | TTC | CGC | AGG | AAC | CTC | 1021 |
| Asn | Pro | Phe | Leu | Tyr | Ala | Phe | Leu | Asp | Ala | Ser | Phe | Arg | Arg | Asn | Leu |
| | | 305 | | | | | 310 | | | | | 315 | | | |
| CGC | CAG | CTG | ATA | ACT | TGC | CGC | GCG | GCA | GCC | TGA | | | | | | 1054 |
| Arg | Gln | Leu | Ile | Thr | Cys | Arg | Ala | Ala | Ala | | | | | | |

( 2 ) INFORMATION FOR SEQ ID NO:2:

( i ) SEQUENCE CHARACTERISTICS:
        ( A ) LENGTH: 328 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Asn Ala Ser Phe Ser Glu Pro Trp Pro Ala Asn Ala Ser Gly
 1               5                  10                  15
Pro Asp Pro Ala Leu Ser Cys Ser Asn Ala Ser Thr Leu Ala Pro Leu
            20                  25                  30
Pro Ala Pro Leu Ala Val Ala Val Pro Val Val Tyr Ala Val Ile Cys
            35                  40                  45
Ala Val Gly Leu Ala Gly Asn Ser Ala Val Leu Tyr Val Leu Leu Arg
    50                  55                  60
Ala Pro Arg Met Lys Thr Val Thr Asn Leu Phe Ile Leu Asn Leu Ala
65                  70                  75                  80
Ile Ala Asp Glu Leu Phe Thr Leu Val Leu Pro Ile Asn Ile Ala Asp
                85                  90                  95
Phe Leu Leu Arg Gln Trp Pro Phe Gly Glu Leu Met Cys Lys Leu Ile
            100                 105                 110
Val Ala Ile Asp Gln Tyr Asn Thr Phe Ser Ser Leu Tyr Phe Leu Thr
            115                 120                 125
Val Met Ser Ala Asp Arg Tyr Leu Val Val Leu Ala Thr Ala Glu Ser
    130                 135                 140
Arg Arg Val Ala Gly Arg Thr Tyr Ser Ala Ala Arg Ala Val Ser Leu
145                 150                 155                 160
Ala Val Trp Gly Ile Val Thr Leu Val Val Leu Pro Phe Ala Val Phe
                165                 170                 175
Ala Arg Leu Asp Asp Glu Gln Gly Arg Arg Gln Cys Val Leu Val Phe
            180                 185                 190
Pro Gln Pro Glu Ala Phe Trp Trp Arg Ala Ser Arg Leu Tyr Thr Leu
            195                 200                 205
Val Leu Gly Phe Ala Ile Pro Val Ser Thr Ile Cys Val Leu Tyr Thr
    210                 215                 220
Thr Leu Leu Cys Arg Leu His Ala Met Arg Leu Asp Ser His Ala Lys
225                 230                 235                 240
Ala Leu Glu Arg Ala Lys Lys Arg Val Thr Phe Leu Val Val Ala Ile
                245                 250                 255
Leu Ala Val Cys Leu Leu Cys Trp Thr Pro Tyr His Leu Ser Thr Val
            260                 265                 270
Val Ala Leu Thr Thr Asp Leu Pro Gln Thr Pro Leu Val Ile Ala Ile
            275                 280                 285
Ser Tyr Phe Ile Thr Ser Leu Thr Tyr Ala Asn Ser Cys Leu Asn Pro
    290                 295                 300
Phe Leu Tyr Ala Phe Leu Asp Ala Ser Phe Arg Arg Asn Leu Arg Gln
305                 310                 315                 320
Leu Ile Thr Cys Arg Ala Ala Ala
                325
```

( 2 ) INFORMATION FOR SEQ ID NO:3:

( i ) SEQUENCE CHARACTERISTICS:
  ( A ) LENGTH: 1518 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 349..1347

( x i ) SEQUENCE DESCRIPTION: SEQ ID NO:3:

```
TCCACTAGTA ACGGCCGCCA GGATCCACAT CTCTTCCCAG GAGGGTGGCC AGCAGCTGCT      60

CTCTGCGGGA GGAGGGAACT GATCTGCTGA AGTCTCACCA GGAAGAGGCG GGAAGGCCCC     120

CACACACCCC ACCAGGCTCC CTCTGGCCCC ATGTCCTTGA CCTGGCAAAG TGGCCGCAGT     180

CTCTGCCAGA GAACCTGGAG TGGCTGTGCC TAACAGACGG CTGGATCTCA AAGTCTCTGG     240

TTGTTTTTCT TTCCTAGAAT CCAGCCTAAG GAGGCCCCCA ACCAGATACC CAACTCCAAG     300

GCACCTCCCA CCTGCCCAGG GCGCAAATCG TCAACGGTCC CAGCTACA  ATG CAG GCC     357
                                                     Met Gln Ala
                                                      1

GCT GGG CAC CCA GAG CCC CTT GAC AGC AGG GGC TCC TTC TCC CTC CCC      405
Ala Gly His Pro Glu Pro Leu Asp Ser Arg Gly Ser Phe Ser Leu Pro
     5              10                  15

ACG ATG GGT GCC AAC GTC TCT CAG GAC AAT GGC ACT GGC CAC AAT GCC      453
Thr Met Gly Ala Asn Val Ser Gln Asp Asn Gly Thr Gly His Asn Ala
 20              25                  30                  35

ACC TTC TCC GAG CCA CTG CCG TTC CTC TAT GTG CTC CTG CCC GCC GTG      501
Thr Phe Ser Glu Pro Leu Pro Phe Leu Tyr Val Leu Leu Pro Ala Val
             40                  45                  50

TAC TCC GGG ATC TGT GCT GTG GGG CTG ACT GGC AAC ACG GCC GTC ATC      549
Tyr Ser Gly Ile Cys Ala Val Gly Leu Thr Gly Asn Thr Ala Val Ile
         55                  60                  65

CTT GTA ATC CTA AGG GCG CCC AAG ATG AAG ACG GTG ACC AAC GTG TTC      597
Leu Val Ile Leu Arg Ala Pro Lys Met Lys Thr Val Thr Asn Val Phe
             70                  75                  80

ATC CTG AAC CTG GCC GTC GCC GAC GGG CTC TTC ACG CTG GTA CTG CCC      645
Ile Leu Asn Leu Ala Val Ala Asp Gly Leu Phe Thr Leu Val Leu Pro
 85                  90                  95

GTC AAC ATC GCG GAG CAC CTG CTG CAG TAC TGG CCC TTC GGG GAG CTG      693
Val Asn Ile Ala Glu His Leu Leu Gln Tyr Trp Pro Phe Gly Glu Leu
100                 105                 110                 115

CTC TGC AAG CTG GTG CTG GCC GTC GAC CAC TAC AAC ATC TTC TCC AGC      741
Leu Cys Lys Leu Val Leu Ala Val Asp His Tyr Asn Ile Phe Ser Ser
                 120                 125                 130

ATC TAC TTC CTA GCC GTG ATG AGC GTG GAC CGA TAC CTG GTG GTG CTG      789
Ile Tyr Phe Leu Ala Val Met Ser Val Asp Arg Tyr Leu Val Val Leu
                 135                 140                 145

GCC ACC GTG AGG TCC CGC CAC ATG CCC TGG CGC ACC TAC CGG GGG GCG      837
Ala Thr Val Arg Ser Arg His Met Pro Trp Arg Thr Tyr Arg Gly Ala
             150                 155                 160

AAG GTC GCC AGC CTG TGT GTC TGG CTG GGC GTC ACG GTC CTG GTT CTG      885
Lys Val Ala Ser Leu Cys Val Trp Leu Gly Val Thr Val Leu Val Leu
165                 170                 175

CCC TTC TTC TCT TTC GCT GGC GTC TAC AGC AAC GAG CTG CAG GTC CCA      933
Pro Phe Phe Ser Phe Ala Gly Val Tyr Ser Asn Glu Leu Gln Val Pro
180                 185                 190                 195

AGC TGT GGG CTG AGC TTC CCG TGG CCC GAG CGG GTC TGG TTC AAG GCC      981
Ser Cys Gly Leu Ser Phe Pro Trp Pro Glu Arg Val Trp Phe Lys Ala
                 200                 205                 210
```

| | | | | | | | | | | | | | | | | |
|---|---|---|---|---|---|---|---|---|---|---|---|---|---|---|---|---|
| AGC | CGT | GTC | TAC | ACT | TTG | GTC | CTG | GGC | TTC | GTG | CTG | CCC | GTG | TGC | ACC | 1029 |
| Ser | Arg | Val | Tyr | Thr | Leu | Val | Leu | Gly | Phe | Val | Leu | Pro | Val | Cys | Thr | |
| | | | 215 | | | | 220 | | | | | 225 | | | | |
| ATC | TGT | GTG | CTC | TAC | ACA | GAC | CTC | CTG | CGC | AGG | CTG | CGG | GCC | GTG | CGG | 1077 |
| Ile | Cys | Val | Leu | Tyr | Thr | Asp | Leu | Leu | Arg | Arg | Leu | Arg | Ala | Val | Arg | |
| | | 230 | | | | 235 | | | | | 240 | | | | | |
| CTC | CGC | TCT | GGA | GCC | AAG | GCT | CTA | GGC | AAG | GCC | AGG | CGG | AAG | GTG | ACC | 1125 |
| Leu | Arg | Ser | Gly | Ala | Lys | Ala | Leu | Gly | Lys | Ala | Arg | Arg | Lys | Val | Thr | |
| | 245 | | | | | 250 | | | | | 255 | | | | | |
| GTC | CTG | GTC | CTC | GTC | GTG | CTG | GCC | GTG | TGC | CTC | CTC | TGC | TGG | ACG | CCC | 1173 |
| Val | Leu | Val | Leu | Val | Val | Leu | Ala | Val | Cys | Leu | Leu | Cys | Trp | Thr | Pro | |
| 260 | | | | | 265 | | | | | 270 | | | | | 275 | |
| TTC | CAC | CTG | GCC | TCT | GTC | GTG | GCC | CTG | ACC | ACG | GAC | CTG | CCC | CAG | ACC | 1221 |
| Phe | His | Leu | Ala | Ser | Val | Val | Ala | Leu | Thr | Thr | Asp | Leu | Pro | Gln | Thr | |
| | | | | 280 | | | | | 285 | | | | | 290 | | |
| CCA | CTG | GTC | ATC | AGT | ATG | TCC | TAC | GTC | ATC | ACC | AGC | CTC | ACG | TAC | GCC | 1269 |
| Pro | Leu | Val | Ile | Ser | Met | Ser | Tyr | Val | Ile | Thr | Ser | Leu | Thr | Tyr | Ala | |
| | | | 295 | | | | 300 | | | | | 305 | | | | |
| AAC | TCG | TGC | CTG | AAC | CCC | TTC | CTC | TAC | GCC | TTT | CTA | GAT | GAC | AAC | TTC | 1317 |
| Asn | Ser | Cys | Leu | Asn | Pro | Phe | Leu | Tyr | Ala | Phe | Leu | Asp | Asp | Asn | Phe | |
| | | 310 | | | | 315 | | | | | 320 | | | | | |
| CGG | AAG | AAC | TTC | CGC | AGC | ATA | TTG | CGG | TGC | TGAAGGGCCT | | GGGCACCATC | | | | 1367 |
| Arg | Lys | Asn | Phe | Arg | Ser | Ile | Leu | Arg | Cys | | | | | | | |
| | 325 | | | | | 330 | | | | | | | | | | |

ATCCCCATCA TCATCATCAC CCCCATCATC ATCACCCCCA CCATTACCCC CATCGTCACG 1427

CCCATCATCA CGCCCATCAT CACCCCCCAT CATCACCCCC ATCATCATGC CCATCATCAC 1487

CCCCCATCAT CATCATGCCC ACCCCTCATC A 1518

( 2 ) INFORMATION FOR SEQ ID NO:4:

( i ) SEQUENCE CHARACTERISTICS:
    ( A ) LENGTH: 333 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Gln | Ala | Ala | Gly | His | Pro | Glu | Pro | Leu | Asp | Ser | Arg | Gly | Ser | Phe |
| 1 | | | | 5 | | | | | 10 | | | | | 15 | |
| Ser | Leu | Pro | Thr | Met | Gly | Ala | Asn | Val | Ser | Gln | Asp | Asn | Gly | Thr | Gly |
| | | | 20 | | | | | 25 | | | | | 30 | | |
| His | Asn | Ala | Thr | Phe | Ser | Glu | Pro | Leu | Pro | Phe | Leu | Tyr | Val | Leu | Leu |
| | | | 35 | | | | 40 | | | | | 45 | | | |
| Pro | Ala | Val | Tyr | Ser | Gly | Ile | Cys | Ala | Val | Gly | Leu | Thr | Gly | Asn | Thr |
| | 50 | | | | | 55 | | | | | 60 | | | | |
| Ala | Val | Ile | Leu | Val | Ile | Leu | Arg | Ala | Pro | Lys | Met | Lys | Thr | Val | Thr |
| 65 | | | | | 70 | | | | | 75 | | | | | 80 |
| Asn | Val | Phe | Ile | Leu | Asn | Leu | Ala | Val | Ala | Asp | Gly | Leu | Phe | Thr | Leu |
| | | | | 85 | | | | | 90 | | | | | 95 | |
| Val | Leu | Pro | Val | Asn | Ile | Ala | Glu | His | Leu | Leu | Gln | Tyr | Trp | Pro | Phe |
| | | | 100 | | | | | 105 | | | | | 110 | | |
| Gly | Glu | Leu | Leu | Cys | Lys | Leu | Val | Leu | Ala | Val | Asp | His | Tyr | Asn | Ile |
| | | 115 | | | | | 120 | | | | | 125 | | | |
| Phe | Ser | Ser | Ile | Tyr | Phe | Leu | Ala | Val | Met | Ser | Val | Asp | Arg | Tyr | Leu |
| | 130 | | | | | 135 | | | | | 140 | | | | |
| Val | Val | Leu | Ala | Thr | Val | Arg | Ser | Arg | His | Met | Pro | Trp | Arg | Thr | Tyr |
| 145 | | | | | 150 | | | | | 155 | | | | | 160 |

-continued

| | | | | | | | | | | | | | | | |
|---|---|---|---|---|---|---|---|---|---|---|---|---|---|---|---|
|Arg|Gly|Ala|Lys|Val 165|Ala|Ser|Leu|Cys|Val 170|Trp|Leu|Gly|Val|Thr 175|Val|
|Leu|Val|Leu|Pro 180|Phe|Phe|Ser|Phe|Ala 185|Gly|Val|Tyr|Ser|Asn 190|Glu|Leu|
|Gln|Val|Pro 195|Ser|Cys|Gly|Leu|Ser 200|Phe|Pro|Trp|Pro|Glu 205|Arg|Val|Trp|
|Phe|Lys 210|Ala|Ser|Arg|Val|Tyr 215|Thr|Leu|Val|Leu|Gly 220|Phe|Val|Leu|Pro|
|Val 225|Cys|Thr|Ile|Cys|Val 230|Leu|Tyr|Thr|Asp|Leu 235|Leu|Arg|Arg|Leu|Arg 240|
|Ala|Val|Arg|Leu|Arg 245|Ser|Gly|Ala|Lys|Ala 250|Leu|Gly|Lys|Ala|Arg 255|Arg|
|Lys|Val|Thr|Val 260|Leu|Val|Leu|Val|Val 265|Leu|Ala|Val|Cys|Leu 270|Leu|Cys|
|Trp|Thr|Pro 275|Phe|His|Leu|Ala|Ser 280|Val|Val|Ala|Leu|Thr 285|Thr|Asp|Leu|
|Pro|Gln 290|Thr|Pro|Leu|Val|Ile 295|Ser|Met|Ser|Tyr|Val 300|Ile|Thr|Ser|Leu|
|Thr 305|Tyr|Ala|Asn|Ser|Cys 310|Leu|Asn|Pro|Phe|Leu 315|Tyr|Ala|Phe|Leu|Asp 320|
|Asp|Asn|Phe|Arg|Lys 325|Asn|Phe|Arg|Ser|Ile 330|Leu|Arg|Cys| | | |

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CCTCACCRTG ATSAGCDTSG AYCGMTA        27

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GAAGGCRTAB AGRAYVGGRT T        21

NUCLEIC ACID ENCODING OPIOID RECEPTOR

FIELD OF THE INVENTION

This invention relates generally to compositions of and methods for obtaining epsilon opioid receptors. The invention relates as well to the DNA sequences encoding epsilon opioid receptors, the recombinant vectors carrying those sequences, the recombinant host cells including either the sequences or vectors, and recombinant epsilon opioid receptor polypeptides. The invention includes as well methods for using the isolated, recombinant receptor polypeptides in assays designed to select and improve among candidate substances such as agonists and antagonists of epsilon opioid receptors and polypeptides for use in diagnostic, drug design and therapeutic applications.

BACKGROUND OF THE INVENTION

Opioid drugs have various effects on perception of pain, consciousness, motor control, mood, and autonomic function and can also induce physical dependence (Koob et al., 1992). The endogenous opioid system plays an important role in modulating endocrine, cardiovascular, respiratory, gastrointestinal and immune functions (Olson et al., 1989). Opioids exert their actions by binding to specific membrane-associated receptors located throughout the central and peripheral nervous system (Pert et al., 1973). The endogenous ligands of these opioid receptors have been identified as a family of more than 20 opioid peptides that derive from the three precursor proteins proopiomelanocortin, proenkephalin, and prodynorphin (Hughes et al., 1975; Akil, et al., 1984). Although the opioid peptides belong to a class of molecules distinct from the opioid alkaloids, they share common structural features including a positive charge juxtaposed with an aromatic ring that is required for interaction with the receptor (Bradbury et al., 1976).

Pharmacological studies have suggested that there are numerous classes of opioid receptors, including those designated δ, κ, μ and ε (Simon, 1991; Lutz et al., 1992). The classes differ in their affinity for various opioid ligands and in their cellular distribution. The different classes of opioid receptors are believed to serve different physiological functions (Olson. et al., 1989; Simon, 1991; Lutz and Pfister, 1992). However, there is substantial overlap of function as well as of distribution. Biochemical characterization of opioid receptors from many groups reports a molecular mass of ≈60,000 Da for all three subtypes, suggesting that they could be related molecules (Loh et at., 1990). Moreover, the similarity between the three receptor subtypes is supported by the isolation of (i) anti-idiotypic monoclonal antibodies competing with both μ and δ ligands but not competing with κ ligands (Gramsch et al., 1988; Coscia et al., 1991) and (ii) a monoclonal antibody raised against the purified μ receptor that interacts with both μ and κ receptors (Bero et al., 1988).

Morphine interacts principally with μ receptors and peripheral administration of this opioid induces release of enkephalins (Bertolucci et al., 1992). The δ receptors bind with the greatest affinity to enkephalins and have a more discrete distribution in the brain than either μ or κ receptors, with high concentrations in the basal ganglia and limbic regions. Thus, enkephalins may mediate part of the physiological response to morphine, presumably by interacting with δ receptors. Despite pharmacological and physiological heterogeneity, at least some types of opioid receptors inhibit adenylate cyclase, increase $K^+$ conductance, and inactivate $Ca^{2+}$ channels through a pertussis toxin-sensitive mechanism (Puttfarcken et al., 1988; Attali et al., 1989, Hsia et al., 1984). These results and others suggest that opioid receptors belong to the large family of cell surface receptors that signal through G proteins (Di Chiara et al., 1992; Loh et al., 1990).

The 6, 7 benzoinorphans such as ethylketocyclazocine label two populations of non-μ, non-δ opioid binding sites in brain that are the κ and ε sites (Chang et al., 1981). The benezencacctamide U-69, 593 has been shown to selectively label one of these two 6, 7 benzoinorphan sites which corresponds to the κ opioid receptor site, but the other benzoinorphan site lacks a selective ligand (Nock et al., 1988). The nature and designation of the U-69, 593 insensitive benzoinorphan site has been debated, including suggestions that it might be a κ opioid receptor subtype because of high affinity interactions with certain κ opioid ligands. However dynorpyhin and other prodymorphin derived peptides presumed to be the endogenous ligands of the κ opioid receptor had very low affinity for this site, which had high affinity for β endorphin (Nock et al., 1993). This pharmacological selectivity profile corresponds to that of the epsilon (ε) opioid receptor, characterized as a dynorphin-insensitive, non-μ, non-δ opioid binding site. The ε receptor was first hypothesized to exist based on bioassays involving the rat vas deferens and from radioligand binding studies in brain; however it has subsequently been shown to be the most abundant opioid binding site in brain (Nock et al., 1993).

Several attempts to clone cDNAs encoding opioid receptors have been reported. A cDNA encoding an opioid-binding protein (OBCAM) with μ selectivity was isolated (Schofield et al., 1989), but the predicted protein lacks transmembrane domains, presumed necessary for signal transduction. More recently, the isolation of another cDNA was reported, which was obtained by expression cloning (Xie et al., 1992). The deduced protein sequence displays seven putative transmembrane domains and is very similar to the human neuromedin K receptor. However, the affinity of opioid ligands for this receptor expressed in COS cells is two orders of magnitude below the expected value, and no subtype selectivity can be shown.

Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic (and potentially α-helical) segments that span the lipid bilayer (Dohlman et al., 1987; Dohlman et al., 1991).

G proteins consist of three tightly associated subunits, α, β and γ (1:1:1) in order of decreasing mass. Following agonist binding to the receptor, a conformational change is transmitted to the G protein, which causes the Gα-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of many catalytic cycles of the effector.

The family of regulatory G proteins comprises a multiplicity of different α-subunits (greater than twenty in man), which associate with a smaller pool of β- and γ-subunits (greater than four each) (Strothman and Simon, 1991). Thus, it is anticipated that differences in the α-subunits probably distinguish the various G protein oligomers, although the targeting or function of the various α-subunits might also depend on the βγ subunits with which they associate (Strothman and Simon, 1991).

Improvements in cell culture and in pharmacological methods, and more recently, use of molecular cloning and gene expression techniques have led to the identification and characterization of many seven-transmembrane segment receptors, including new sub-types and sub-sub-types of previously identified receptors. The $\alpha_1$ and $\alpha_2$-adrenergic receptors once thought to each consist of single receptor species, are now known to each be encoded by at least three distinct genes (Kobilka et al., 1987; Regan et al., 1988; Cotecchia et al., 1988; Lomashey, 1990). In addition to rhodopsin in rod cells, which mediates vision in dim light, three highly similar cone pigments mediating color vision have been cloned (Nathans et al., 1986A, and Nathans et al., 1986B). All of the family of G protein-coupled receptors appear to be similar to other members of the family of G protein-coupled receptors (e.g., dopaminergic, muscarinic, serotonergic, tachykinin, etc.), and each appears to share the characteristic seven-transmembrane segment topography.

When comparing the seven-transmembrane segment receptors with one another, a discernible pattern of amine acid sequence conservation is observed. Transmembrane domains are often the most similar, whereas the amine and carboxyl terminal regions and the cytoplasmic loop connecting transmembrane segments V and VI can be quite divergent (Dohlman et al., 1987).

Interaction with cytoplasmic polypeptides, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al., 1991).

With the growing number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple functionally distinct receptor sub-types. Moreover, G proteins with similar receptor and effector coupling specificities have also been identified. For example, three species of human $G_i$ have been cloned (Itoh et al., 1988), and alternate mRNA splicing has been shown to result in multiple variants of $G_S$ (Kozasa et al., 1988). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini et al., 1989). For rhodopsin, muscarinic, and β-adrenergic receptors, two conserved cysteine residues in each of the two first extracellular loops have been shown critical for stabilizing the functional protein structure and are presumed to do so by forming a disulfide bridge. Structure/function studies of opioid ligands have shown the importance of a protonated amine group for binding to the receptor with high affinity. The binding site of the receptor might, therefore, possess a critical negatively charged counterpart. Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances do specific subtype and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al., 1988; Payette et al., 1990; King et al., 1990).

One such system was recently developed in yeast cells, in which the genes for a mammalian $\beta_2$-adrenergic receptor and $G_s$ α-subunit were coexpressed (King et al., 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUS1) fused to the *Escherichia coli* lac Z gene (encoding β-galactosidase) (King et al., 1990).

Finally, expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it is possible to address the heretofore intractable problems associated with design and testing of isoform-specific opioid receptor agonists and antagonists. The availability of cDNAS encoding the opioid receptors will permit detailed studies of signal-transduction mechanisms and reveal the anatomical distribution of the mRNAs of these receptors, providing information on their expression pattern in the nervous system. This information should ultimately allow better understanding of the opioid system in analgesia, and also the design of more specific therapeutic drugs.

Availability of polynucleotide sequences encoding opioid receptors, and the polypeptide sequences of the encoded receptors, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods tier screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected tier further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only one receptor subtype is expressed exclusively. With traditional prior art screens you are basically looking at the wrong interactions or, at best, the proper interactions mixed in with a whole variety of unwanted interactions. An additional fundamental deficiency of animal tissue screens is that they contain animal receptors—ideal for the development of drugs for animals but of dubious value in human therapeutic agents.

The disadvantages of the prior art may be overcome by providing a polynucleotide transfected into suitable host cells which can express polypeptide sequences corresponding to opioid receptors, both in large quantities and through relatively simple laboratory procedures. The result is the availability of extremely specific receptor-drug interactions free from the competitive and unwanted interactions encountered in tissue-based screens. Further expression in a microorganism where no such endogenous receptors exist (e.g. yeast cells or mutant mammalian cell lines) can be useful for screening and evaluating sub-type-selective drugs (Marullo et al., 1988; Paycite et al., 1990; and King et al., 1990).

BRIEF SUMMARY OF THE INVENTION

In one aspect, the present invention provides an isolated and purified polynucleotide that encodes an epsilon opioid receptor polypeptide. In a preferred embodiment, a polynucleotide of the present invention is a DNA molecule. Even more preferred, a polynucleotide of the present invention encodes a polypeptide comprising the amino acid residue sequence of SEQ ID NO: 2 or SEQ ID NO: 4. Most preferably, an isolated and purified polynucleotide of the invention comprises the nucleotide base sequence of SEQ ID NO: 1 or SEQ ID NO: 3.

Yet another aspect of the present invention contemplates an isolated and purified polynucleotide comprising a base sequence that is identical or complementary to a segment of at least 10 contiguous bases of SEQ ID NO: 1 or SEQ ID NO: 3, wherein the polynucleotide hybridizes to a polynucleotide that encodes an epsilon opioid receptor polypeptide. Preferably, an isolated and purified polynucleotide comprises a base sequence that is identical or complementary to a segment of at least 25 to 70 contiguous bases of SEQ ID NO: 1 or SEQ ID NO: 3. For example, a polynucleotide of the invention can comprise a segment of bases identical or complementary to 40 to 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO: 1 or SEQ ID NO: 3. The polynucleotide of the invention hybridizes to SEQ ID NO: 1 or SEQ ID NO: 3, or a complement of SEQ ID NO: 1 or SEQ ID NO: 3. Preferably, the isolated and purified polynucleotide comprises a base sequence that is identical or complementary to a segment of at least 25 to 70 contiguous bases of SEQ ID NO: 1 or SEQ ID NO: 3. For example, the polynucleotide of the invention can comprise a segment of bases identical or complementary to 40 to 55 contiguous bases of SEQ ID NO: 1 or SEQ ID NO: 3.

In another embodiment, the present invention contemplates an isolated and purified epsilon opioid receptor polypeptide. Preferably, a polypeptide of the invention is a recombinant polypeptide. Even more preferably, an epsilon opioid receptor polypeptide of the present invention comprises the amino acid residue sequence of SEQ ID NO: 2 or SEQ ID NO: 4.

In an alternative embodiment, the present invention provides an expression vector comprising a polynucleotide that encodes an epsilon opioid receptor polypeptide. Preferably, an expression vector of the present invention comprises a polynucleotide that encodes a polypeptide comprising the amino acid residue sequence of SEQ ID NO: 2 or SEQ ID NO: 4. More preferably, an expression vector of the present invention comprises a polynucleotide comprising the nucleotide base sequence of SEQ ID NO: 1 or SEQ ID NO: 3. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxyl-terminal amino acid and within a transcriptional unit of the encoded polypeptide.

In yet another embodiment, the present invention provides a recombinant host cell transfected with a polynucleotide that encodes an epsilon opioid receptor polypeptide. Preferably, a recombinant host cell of the present invention is transfected with the polynucleotide of SEQ ID NO: 1 or SEQ ID NO: 3. Even more preferably, a host cell of the invention is a eukaryotic host cell. Still more preferably, a recombinant host cell of the present invention is a yeast cell. Alternatively, a recombinant host cell of the invention is a COS, CHO or BHK cell. In another aspect, a recombinant host cell of the present invention is a prokaryotic host cell. In another embodiment, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of an epsilon opioid receptor polypeptide in a manner to enable all necessary transcriptional and post-transcriptional modification.

In yet another embodiment, the present invention contemplates a process of preparing an epsilon opioid receptor polypeptide comprising transfecting a cell with polynucleotide that encodes an epsilon opioid receptor polypeptide to produce a transformed host cell and maintaining the transformed host cell under biological conditions sufficient for expression of the polypeptide. Preferably, the transformed host cell is a eukaryotic cell. More preferably still, the eukaryotic cell is a COS, CHO or BHK cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO: 1 or SEQ ID NO: 3.

In still another embodiment, the present invention provides an antibody immunoreactive with an epsilon opioid receptor polypeptide. Preferably, an antibody of the invention is a monoclonal antibody. More preferably, an epsilon opioid receptor polypeptide comprises the amino acid residue sequence of SEQ ID NO: 2 or SEQ ID NO: 4.

In another aspect, the present invention contemplates a process of producing an antibody immunoreactive with an epsilon opioid receptor polypeptide comprising the steps of (a) transfecting a recombinant host cell with a polynucleotide that encodes an epsilon opioid receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO: 1 or SEQ ID NO: 3. Alternatively, steps (a), (b) and (c) can be avoided by use of a synthetic polypeptide. Even more preferably, the present invention provides an antibody prepared according to the process described above.

Alternatively, the present invention provides a process of detecting an epsilon opioid receptor polypeptide, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes an epsilon opioid receptor polypeptide, wherein the process comprises (a) hybridizing the messenger RNA transcript with a polynucleotide sequence that encodes the epsilon opioid receptor polypeptide to form a duplex; and (b) detecting the duplex. Alternatively, the present invention provides a process of detecting a DNA molecule that encodes an epsilon opioid receptor polypeptide, wherein the process comprises (a) hybridizing DNA molecules with a polynucleotide that encodes an epsilon opioid receptor polypeptide to form a duplex; and (b) detecting the duplex.

In another aspect, the present invention contemplates a diagnostic assay kit for detecting the presence of an epsilon opioid receptor polypeptide in a biological sample, where the kit comprises a first container containing a first antibody capable of immunoreacting with an epsilon opioid receptor polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes an epsilon opioid receptor polypeptide, the kit comprising a first container that contains a second polynucleotide identical or complementary to a segment of at least 10 contiguous nucleotide bases of SEQ ID NO: 1 or SEQ ID NO: 3.

In another embodiment, the present invention contemplates a diagnostic assay kit for detecting the presence, in a biological sample, of an antibody immunoreactive with an epsilon opioid receptor polypeptide, the kit comprising a first container containing an epsilon opioid receptor polypeptide that immunoreacts with the antibody, with the polypeptide present in an amount sufficient to perform at least one assay.

In yet another aspect, the present invention contemplates a process of screening substances for their ability to interact with an epsilon opioid receptor polypeptide comprising the steps of providing an epsilon opioid receptor polypeptide, and testing the ability of selected substances to interact with the opioid receptor polypeptide.

In a preferred embodiment, providing an epsilon opioid receptor polypeptide is transfecting a host cell with a polynucleotide that encodes an epsilon opioid receptor polypeptide to form a transformed cell and maintaining the transformed cell under biological conditions sufficient for expression of the opioid receptor polypeptide. Preferably, a polynucleotide used to transfect a host cell comprises the nucleotide sequence of SEQ ID NOS: 1 or 3.

BRIEF DESCRIPTION OF THE DRAWINGS

In the drawings which form a portion of the specification:

FIG. 1A, FIG. 1B, FIG. 1C show the nucleotide and deduced amino acid sequences of the human ε receptor designated clone #12 (SEQ ID NOS: 1 and 2).

FIG. 2A, FIG. 2B, FIG. 2C, FIG. 2D show the nucleotide and deduced amino acid sequences of the human ε receptor designated clone #11 (SEQ ID NOS: 3 and 4).

DETAILED DESCRIPTION OF THE INVENTION

I. The Invention

Figure 3A:
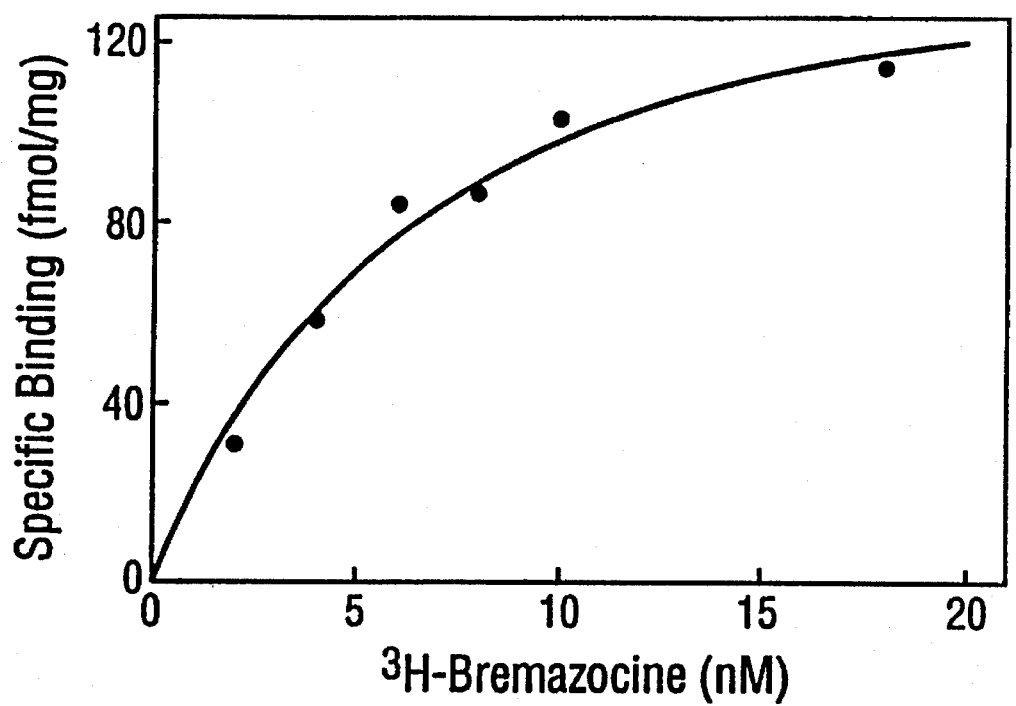
FIG. 3A, FIG. 3B, FIG. 3C show a bremazocine saturation isotherm and competition binding to the ε opioid receptor expressed in BHK cell.
Figure 3B:
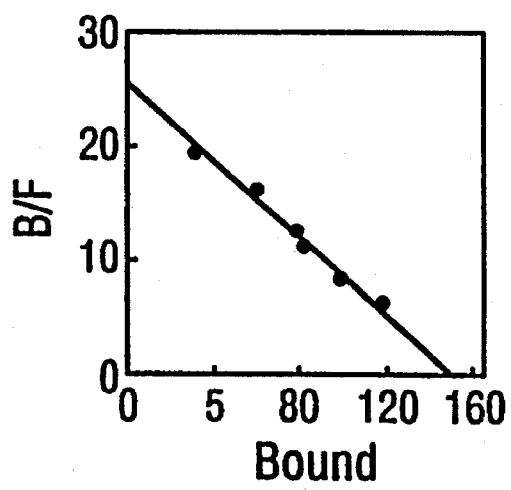
Figure 3C:
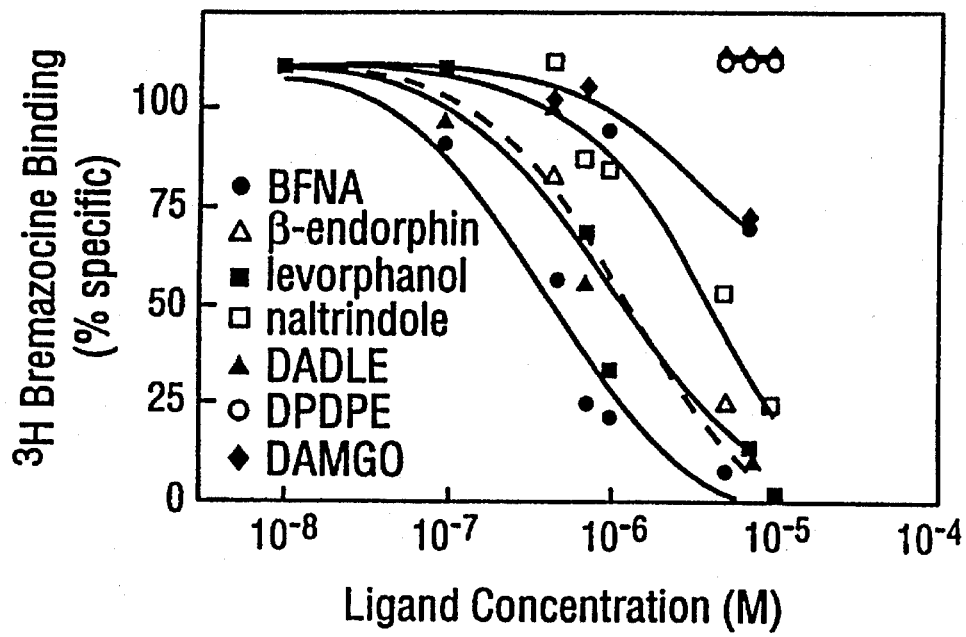
Figure 4:
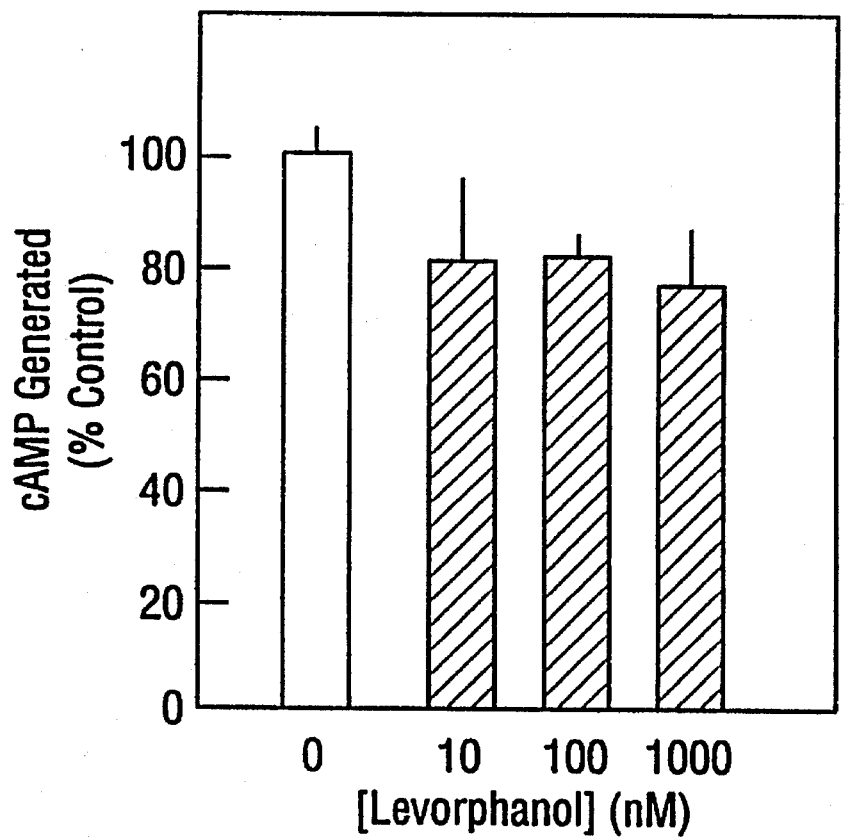
FIG. 4 shows inhibition of cAMP formation by levorphanol in BHK cells expressing ε receptors.

The present invention provides DNA segments, purified polypeptides, methods for obtaining antibodies, methods of cloning and using recombinant host cells necessary to obtain and use recombinant epsilon opioid receptors. Thus, the difficulties encountered with applying the standard approaches of classical genetics or techniques in molecular biology evident in the prior art to epsilon opioid receptors, have been overcome. Accordingly, the present invention concerns generally compositions and methods for the preparation and use of epsilon opioid receptors.

The receptor of the present invention has high affinity for 6,7-benzoinorphans and β-endorphin, but low affinity for the μ, δ and κ opioid receptor ligands, confirming an epsilon (ε) receptor affinity profile. The ε receptor gene, intronless in its coding region, is located on chromosome 10, on q11.2–q21.1, and shares homology to the μ, δ and κ receptor cDNA clone. mRNA encoding the ε receptor was detected in cerebral cortex, frontal cortex, hypothalamus, and pituitary. In situ hybridization histochemistry revealed mRNA transcripts in pituitary that showed selective localization in the lateral wings of the anterior pituitary gland. The cloning and characterization of the human ε receptor provides great impetus to the study of opioid actions, notably that of supraspinal analgesia, hypothesized to be mediated through this receptor.

II. Polynucleotide

A. Isolated and purified polynucleotides that encode epsilon opioid receptor polypeptides.

In one aspect, the present invention provides an isolated and purified polynucleotide that encodes an epsilon opioid receptor polypeptide.

As used herein, the phrase "epsilon opioid receptor" means a receptor that binds opioid and analogues thereof in a manner as described herein. It is readily apparent to one of ordinary skill in the art that, because the classification and denomination of receptors is based in large part on binding studies, the classification or name given a particular receptor is subject to modification as new drugs are developed. The name epsilon opioid receptor is thus used for convenience to categorize the pharmacological behavior of the polypeptide disclosed herein.

In a preferred embodiment, the polynucleotide of the present invention is a DNA molecule. Even more preferred, a polynucleotide of the present invention encodes a polypeptide comprising the amino acid residue sequence of SEQ ID NO: 2 or SEQ ID NO: 4. Most preferably, an isolated and purified polynucleotide of the invention comprises the nucleotide base sequence of SEQ ID NO: 1 or SEQ ID NO: 3.

Several of the rodent opioid receptors (OR) have now been cloned, the δ, κ, and μ (Yasuda et al., 1993 and Chen et al., 1993). Two degenerate oligonucleotides based on the nucleotide sequence encoding the third and seventh transmembrane (TM) regions of the mouse δ opioid receptor were prepared. The gene structure encoding the OR has not yet been reported. Because many previously cloned G protein-coupled receptors are encoded on single exons, those oligonucleotides were used to amplify, in the polymerase chain reaction (PCR) human genomic DNA (Hazum et al., 1979). The amplified DNA (in the size range 500 to 1000 bp) was subcloned into the Bluescript plasmid, and 150 of the resulting clones were sequenced. From the nucleotide sequences obtained it appeared that none of the genomic PCR clones encoded the human orthologues of the rodent OR. One clone, #12, shared identity with the δ, μ and κ ORs. To obtain the full length gene encoded by this PCR-derived fragment (540 bp), a human genomic library was screened and 18 positive clones were obtained from the screening. Rapid PCR analysis of these phage clones with the original PCR oligonucleotides succeeded in identifying one phage which contained the sequence of clone #12. This phage was purified and a fragment (4.5 kb) from this clone was subcloned into the Bluescript plasmid and sequenced.

This genomic clone, named HG-12, contained an intronless reading frame of 981 nucleotides, encoding a 327 amino acid protein (see FIGS. 1A–1C). PCR analysis using two oligonucleotides specific for clone #12 sequence identified identically sized DNA fragments in chimpanzee, monkey, rat and mouse genomic DNA.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding an epsilon opioid receptor polypeptide of the present invention is described hereinafter in Examples 1 and 2. A polynucleotide can also be prepared from genomic DNA libraries using lambda phage technologies.

In another aspect, the present invention provides an isolated and purified polynucleotide that encodes an epsilon opioid receptor polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of SEQ ID NO: 2 or SEQ ID NO: 4. More preferably still, the polynucleotide comprises the nucleotide sequence of SEQ ID NO: 1 or SEQ ID NO: 3.

B. Probes and Primers.

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in SEQ ID NO: 1 or SEQ ID NO: 3. The ability of such nucleic acid probes to specifically hybridize to a polynucleotide encoding an epsilon opioid receptor lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes an epsilon opioid receptor polypeptide from mammalian cells using PCR technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes an epsilon opioid receptor polypeptide, such as that shown in SEQ ID NO: 1 or SEQ ID NO: 3. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO: 1 or SEQ ID NO: 3, wherein the polynucleotide hybridizes to a polynucleotide that encodes an epsilon opioid receptor polypeptide. Preferably, the isolated and purified polynucleotide comprises a base sequence that is identical or complementary to a segment of at least 25 to 70 contiguous bases of SEQ ID NO: 1 or SEQ ID NO: 3. For example, the polynucleotide of the invention can comprise a segment of 35 bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02M–0.15M NaCl at temperatures of 50° C. to 70° C. Those conditions are particularly selective, and tolerate little, if any, mismatch between the probe and the template or target strand.

Of course, for some applications, for example, where one desires to prepare routants employing a mutant primer strand hybridized to an underlying template or where one seeks to isolate an epsilon opioid receptor polypeptide coding sequence from other cells, functional equivalents, or the like, less stringent hybridization conditions are typically needed to allow formation of the heteroduplex. In these circumstances, one can desire to employ conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In still another embodiment of the present invention, there is provided an isolated and purified polynucleotide comprising a base sequence that is identical or complementary to a segment of at least 10 contiguous bases of SEQ ID NO: 1 or SEQ ID NO: 3. The polynucleotide of the invention hybridizes to SEQ ID NO: 1 or SEQ ID NO: 3, or a complement of SEQ ID NO: 1 or SEQ ID NO: 3. Preferably, the isolated and purified polynucleotide comprises a base sequence that is identical or complementary to a segment of at least 25 to 70 contiguous bases of SEQ ID NO: 1 or SEQ ID NO: 3. For example, the polynucleotide of the invention can comprise a segment of bases identical or complementary to 40 to 55 contiguous bases of SEQ ID NO: 1 or SEQ ID NO: 3.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove non-specifically bound probe molecules, specific hybridization is detected, or even quantified, by means of the label.

III. Epsilon Opioid Receptor.

In one embodiment, the present invention contemplates an isolated and purified epsilon opioid receptor polypeptide. Preferably, an epsilon opioid receptor polypeptide of the invention is a recombinant polypeptide. Even more preferably, an epsilon opioid receptor polypeptides of the present invention comprises the amino acid residue sequence of SEQ ID NO: 2 or SEQ ID NO: 4. An epsilon opioid receptor polypeptide preferably comprises less than about 500 amino acid residues and, more preferably less than about 400 amino acid residues.

The deduced amino acid residue of human clone 12 is shown in FIGS. 1A–1C. Hydrophobic analysis of the deduced amino acid sequence demonstrated the seven transmembrane (TM) regions characteristic of the G protein-coupled receptor genes, and overall, the protein sequence most closely resembled the OR. A comparison of the amino acid sequence encoded by HG-12 with previously cloned OR, reveals that amino acids that are identical, and that are conservatively substituted, mostly in the seven putative TM regions. The percentage of amino acids identical with those encoded by HG-12, within transmembrane regions and overall for the entire protein are as follows: δ, 40% and 37%, κ and 43% and 35%. The protein encoded by HG-12 contains three putative glycosylation sites in the amino terminus and consensus sequences for phosphorylation by protein kinase C and protein kinase A. An aspartic acid in the third TM region which is also present in the other OR and the catecholamine receptors may form part of the ligand binding site.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like opioid receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte, J. and R. F. Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (–0.4); threonine (–0.7); serine (–0.8); tryptophan (–0.9); tyrosine (–1.3); proline (–1.6); histidine (–3.2); glutamate (–3.5); glutamine (–3.5); aspartate (–3.5); asparagine (–3.5); lysine (–3.9); and arginine (–4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid call be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (–0.5±1); threonine (–0.4); alanine (–0.5); histidine (–0.5); cysteine (–1.0); methionine (–1.3); valine (–1.5); leucine (–1.8); isoleucine (–1.8); tyrosine (–2.3); phenylalanine (–2.5); tryptophan (–3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of an epsilon opioid receptor polypeptide as set forth above.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of routants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by (Adelman et al., 1983). As will be appreciated, the technique typically employs a phage vector which can exist in both a single stranded and double stranded form. Typical vectors useful in site-directed mutagenesis include vectors such as the M13 phage (Messing et al., 1981). These phages are commercially available and their use is generally known to those of skill in the art.

In general, site-directed mutagenesis in accordance herewith is performed by first obtaining a single-stranded vector which includes within its sequence a DNA sequence which encodes all or a portion of the epsilon opioid receptor polypeptide sequence selected. An oligonucleotide primer bearing the desired mutated sequence is prepared, generally synthetically, for example, by the method of (Crea et al., 1978). This primer is then annealed to the singled-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

Amino acid residues can be added to or deleted from the epsilon opioid receptor polypeptide through the use of standard molecular biological techniques without altering the functionality of the receptor. For example, portions of the epsilon opioid receptor can be removed to create truncated opioid receptors. The truncated receptor retains the properties of epsilon opioid receptors such as ligand binding and the ability to interact with other proteins (G proteins, adenylyl cyclase, for example). Functional truncated proteins have been reported for phosphodiesterases, ion channels, and membrane transporters. As used herein, truncated receptors are receptors in which amino acids have been removed from the wild type receptor to create a shorter receptor or portions thereof. As used herein, chimeric receptors are receptors in which amino acids have been added to the receptor. A chimeric receptor can be shorter, longer or the same length as the wild type receptor.

The functional activity of truncated and chimeric receptors have been demonstrated in a number of receptor systems. In particular, truncated and chimeric adrenergic receptors, which are structurally similar to the opioid receptors, have been shown to retain functional properties of the wild type adrenergic receptor.

Most of the long carboxyl terminus of the avian β-adrenergic receptor can be deleted or proteolytically removed without altering the ligand-binding properties or regulatory properties of the receptor. The ligand binding properties of five truncated B-adrenergic receptors for both agonists and antagonists were found to be similar to those of the wild type receptor. Furthermore, truncated adrenergic receptors also stimulated adenylyl cyclase activity. In fact, truncated β-adrenergic receptors, in the presence of agonists, showed a greater stimulation of adenylyl cyclase activity than the stimulation achieved by the wild type receptor. (Parker et al., 1991).

Similar results were obtained for the α-adrenergic receptor. A truncated α-adrenergic receptor activated phosphatidyl inositol hydrolysis as effectively as wild type α-adrenergic receptor. (Cotecchia et al., 1989).

Functional chimeric receptors have also been created by a number of investigators. Functional chimetic adrenergic receptors were created by splicing together sections of the $\alpha_2$ and $\beta_2$ adrenergic receptors. (Kobilka et al., 1988). Functional chimeras have also been generated for the following receptors: between $\beta_1$ and $\beta_2$ receptors, (Frielle et al., 1988; Marullo et al., 1990); between m2 and m3 muscarinic receptors, (Wess et al. 1990); between m1 muscarinic and β adrenergic receptors, (Wong et al., (1990); between $D_2$ dopamine and m1 muscarinic receptors, (England et al., 1991); between luteinizing hormone and β adrenergic receptors, (Moyle et al., 1991); between $NK_1$ and $NK_3$ substance P receptors, (Gether et al., 1993); and platelet-derived growth factor and epidermal growth factor receptors, (Seedorf et al., 1991).

Chimeric epsilon opioid receptors can be created by splicing sections of a second receptor to an epsilon receptor. The two receptors can be similar to each other. Thus, tier the creation of chimeric epsilon opioid receptors, other opioid receptors, such as sigma, delta, kappa and mu opioid receptors, are ideal sources for nucleotide sequences. For example, a transmembrane domain in the epsilon opioid receptor can be substituted with an analogous transmembrane domain from sigma, delta or kappa opioid receptor. It is contemplated that the nucleotide source of the second receptor is not limited to opioid receptors. Chimeric receptors can be created from epsilon opioid receptor and other similar receptors such as acetylcholine, adenosine, adrenergic, angiotensin, bombazine, bradykinin, cannabinoid, dopamine, endothelin, histamine, interleukin, luteinizing hormone, neuromedin K, neuropeptide Y, odorant, prostaglandin, parathyroid hormone, serotonin, somatostatin, substance K, substance P, thrombin, thromboxane A2, thyrotropin releasing hormone and vasopressin receptors.

An epsilon opioid receptor polypeptide of the present invention is understood not to be limited to a particular source. Thus, the invention provides for the general detection and isolation of the genus of epsilon opioid receptor polypeptides from a variety of sources. It is believed that a number of species of the family of epsilon opioid receptor polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

Opioid receptor polypeptides are found in virtually all mammals including human. As is the case with other receptors, there is likely little variation between the structure and function of an opioid receptor in different species. Where there is a difference between species, identification of those differences is well within the skill of an artisan. Thus, the present invention contemplates an epsilon opioid receptor polypeptide from any mammal. A preferred mammal is a rodent or a human.

III. Expression Vectors

In an alternate embodiment, the present invention provides expression vectors comprising a polynucleotide that encodes an epsilon opioid receptor polypeptide. Preferably, expression vectors of the present invention comprise polynucleotides that encode polypeptides comprising the amino acid residue sequence of SEQ ID NO: 2 or SEQ ID NO: 4. More preferably, expression vectors of the present invention comprise polynucleotides comprising the nucleotide base sequence of SEQ ID NO: 1 or SEQ ID NO: 3. Even more preferably, expression vectors of the invention comprise polynucleotides operatively linked to an enhancer-promoter. More preferably still, expression vectors of the invention comprise a polynucleotide operatively linked to a prokaryotic promoter. Alternatively, expression vectors of the present invention comprise a polynucleotide operatively linked to an enhancer-promoter that is a eukaryotic promoter. Expression vectors further comprise a polyadenylation signal that is positioned 3' of the carboxyl-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well known in the art. A preferred transcription-terminating region is derived from a bovine growth hormone gene.

An expression vector comprises a polynucleotide that encodes an epsilon opioid receptor polypeptide. Such a polypeptide is meant to include a sequence of nucleotide bases encoding an epsilon opioid receptor polypeptide sufficient in length to distinguish said segment from a polynucleotide segment encoding a non-opioid receptor polypeptide. A polypeptide of the invention can also encode biologically functionally equivalent polypeptides or peptides which have variant amino acid sequences, such as with changes selected based on considerations such as the relative hydropathic score of the amino acids being exchanged. These variant sequences are those isolated from natural sources or induced in the sequences disclosed herein using an mutagenic procedure such as site-directed mutagenesis.

Preferably, expression vectors of the present invention comprise polynucleotides that encode polypeptides comprising the amino acid residue sequence of SEQ ID NO: 2 or SEQ ID NO: 4. An expression vector can include an epsilon opioid receptor polypeptide coding region itself of any of the epsilon opioid receptor polypeptides noted above or it can contain coding regions bearing selected alterations or modifications in the basic coding region of such an epsilon opioid receptor polypeptide. Alternatively, such vectors or fragments can code larger polypeptides or polypeptides which nevertheless include the basic coding region. In any event, it should be appreciated that due to codon redundancy as well as biological functional. equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.) and pRc/CMV (Invitrogen, San Diego, Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors can be detected.

A DNA molecule of the present invention can be incorporated into a vector using a number of techniques which are well known in the art. For instance, the vector pUC18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the epsilon opioid receptor polypeptide-encoding DNA itself, and as a means for preparing the encoded polypeptides. It is contemplated that where epsilon opioid receptor polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic epsilon opioid receptor polypeptides are anticipated using the teaching of the disclosed invention, one likely expresses such sequences in eukaryotic hosts. However, even where the DNA segment encodes a eukaryotic epsilon opioid receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the opioid receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the epsilon opioid receptor polypeptide, an appropriate polyadenylation site.

The pRc/CMV vector (available from Invitrogen) is an exemplary vector for expressing an epsilon opioid receptor polypeptide in mammalian cells, particularly COS, CHO and BHK cells. A polypeptide of the present invention under the control of a CMV promoter can be efficiently expressed in mammalian cells.

pCMV vectors are another exemplary vectors. The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindIII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and Bam. HI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis (Jobling et al., 1987), Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha polypeptide, polypeptide phosphatase, synaptophysin, synapsin, insulin receptor, influenza hemagglutinin, androgen receptor, sterol 26-hydroxylase, steroid 17- and 21hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMV that can cause spurious translation initiation. This codon should be avoided if possible in expression plasmids. A paper describing the construction and use of the parenteral pCMV1 and pCMV4 vectors has been published (Anderson et al., 1989b).

IV. Transfected Cells.

In yet another embodiment, the present invention provides recombinant host cells transformed or transfected with a polynucleotide that encodes an epsilon opioid receptor polypeptide, as well as transgenic cells derived from those transformed or transfected cells. Preferably, recombinant host cells of the present invention are transfected with a polynucleotide of SEQ ID NO: 1 or SEQ ID NO: 3. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

A transfected cell can be prokaryotic or eukaryotic. Preferably, the host cells of the invention are eukaryotic host cells. More preferably, the recombinant host cells of the invention are COS cells. Where it is of interest to produce a human epsilon opioid receptor polypeptides, cultured mammalian or human cells are of particular interest.

In another aspect, the recombinant host cells of the present invention are prokaryotic host cells. Preferably, the recombinant host cells of the invention are bacterial cells of the DH5α strain of *Escherichia coli*. In general, prokaryotes are preferred for the initial cloning of DNA sequences and constructing the vectors useful in the invention. For example, *E. coli* K12 strains can be particularly use/id. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratus marcesans*, and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang et al., 1978; Itakura et al., 1977, Goeddel et al., 1979, Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist et al., 1980).

In addition to prokaryotes, eukaryotic microbes, such as yeast can also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for an mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellar organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments can also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing a Recombinant Epsilon Opioid Receptor Polypeptide.

In yet another embodiment, the present invention contemplates a process of preparing an epsilon opioid receptor polypeptide comprising transfecting cells with a polynucleotide that encodes an epsilon opioid receptor polypeptide to produce transformed host cells; and maintaining the transformed host cells under biological conditions sufficient for expression of the polypeptide. Preferably, the transformed host cells are eukaryotic cells. More preferably still, the eukaryotic cells are COS or BHK cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO: 1 or SEQ ID NO: 3. Most preferably, transfection is accomplished using a hereinbefore disclosed expression vector.

A host cell used in the process is capable of expressing a functional, recombinant epsilon opioid receptor polypeptide. A preferred host cell is a Chinese hamster ovary cell or a baby hamster kidney cell. However, a variety of cells are amenable to a process of the invention, for instance, yeasts cells, human cell lines, and other eukaryotic cell lines known well to those of the art.

Following transfection, the cell is maintained under culture conditions for a period of time sufficient for expression of an epsilon opioid receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of an epsilon opioid receptor polypeptide. A suitable time depends inter alia upon the cell type used and is readily determinable by a skilled artisan. Typically, maintenance time is from about 2 to about 14 days.

A recombinant epsilon opioid receptor polypeptide is recovered or collected either from the transfected cells or the medium in which those cells are cultured. Recovery comprises isolating and purifying the recombinant polypeptide. Isolation and purification techniques for polypeptides are well known in the art and include such procedures as precipitation, filtration, chromatography, electrophoresis and the like.

VI. Antibodies.

In still another embodiment, the present invention provides antibodies immunoreactive with a polypeptide of the present invention. Preferably, the antibodies of the invention are monoclonal antibodies. More preferably, the polypeptide comprises the amino acid residue sequence of SEQ ID NO: 2 or SEQ ID NO: 4. Means for preparing and characterizing antibodies are well known in the art (See, e.g., Harlow E. and D. Lane, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobenzoyl-N-hydroxysuccinimide ester, carbodiimide and bis-biazotized benzidine.

As is also well known in the art, immuogencity to a particular immunogen can be enhanced by the use of nonspecific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with an epsilon opioid receptor polypeptide comprising the steps of (a) transfecting recombinant host cells with polynucleotide that encodes an epsilon opioid receptor polypeptide; (b) culturing the host cells under conditions sufficient for expression of the polypeptide; (c) recovering the polypeptide; and (d) preparing the antibodies to the polypeptide. Preferably, the host cell is transfected with the polynucleotide of SEQ ID NO: 1 or SEQ ID NO: 3. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is an murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de nova synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thyroidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera tittered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

VII. Pharmaceutical Compositions.

In a preferred embodiment, the present invention provides pharmaceutical compositions comprising an epsilon opioid receptor polypeptide and a physiologically acceptable carrier. More preferably, a pharmaceutical composition comprises an epsilon opioid receptor polypeptide having the amino acid residue sequence of SEQ ID NO: 2 or SEQ ID NO: 4. Even more preferably, a pharmaceutical composition of the invention comprises a polynucleotide that encodes an epsilon opioid receptor polypeptide and a physiologically acceptable carrier. Still more preferably, a pharmaceutical composition of the present invention comprises the amino acid residue sequence of SEQ ID NO: 2 or SEQ ID NO: 4. Alternatively, a pharmaceutical composition comprises the nucleotide sequence of SEQ ID NO: 1 or SEQ ID NO: 3.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon, et al., 1990; Ferruti, et al., 1986; and Ranade, V. V., 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

VIII. A Process of Detecting Polynucleotide and the Polypeptides Encoded.

Alternatively, the present invention provides a process of detecting a polypeptide of the present invention, wherein the process comprises immunereacting the polypeptide with antibodies prepared according to a process described above to form an antibody-polypeptide conjugate and detecting the conjugates.

In yet another embodiment, the present invention contemplates a process of detecting a messenger RNA transcript that encodes an epsilon opioid receptor polypeptide, wherein the process comprises (a) hybridizing the messenger RNA transcript with a polynucleotide sequence that encodes the polypeptide to form a duplex; and (b) detecting the duplex. Alternatively, the present invention provides a process of detecting a DNA molecule that encodes an epsilon opioid receptor polypeptide, wherein the process comprises (a) hybridizing DNA molecules with a polynucleotide that encodes an epsilon opioid receptor polypeptide to form a duplex; and (b) detecting the duplex.

IX. Screening Assays

In yet another aspect, the present invention contemplates a process of screening substances for their ability to interact with an epsilon opioid receptor polypeptide, the process comprising the steps of providing a polypeptide of the present invention and testing the ability of selected substances to interact with that polypeptide.

Utilizing the methods and compositions of the present invention, screening assays for the testing of candidate substances such as agonists and antagonists of epsilon opioid receptors can be derived. A candidate substance is a substance which can interact with or modulate, by binding or other intramolecular interaction, an epsilon opioid receptor polypeptide. In some instances, such a candidate substance is an agonist of the receptor and in other instances can exhibit antagonistic attributes when interacting with the receptor polypeptide. In other instances, such substances have mixed agonistic and antagonistic properties or can modulate the receptor in other ways. Alternatively, such substances can promote or inhibit transcription of an epsilon opioid receptor.

Recombinant receptor expression systems of the present invention possess definite advantages over tissue-based systems. The methods of the present invention make it possible to produce large quantities of epsilon opioid receptors for use in screening assays. More important, however, is the relative purity of the receptor polypeptides provided by the present invention. A relatively pure polypeptide preparation for assaying a protein-protein interaction makes it possible to use elusive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest were the source of the receptor. Alternatively, investigators homogenized the tissue and used the crude homogenate as a receptor source. A major difficulty with this approach is that there are no tissue types where only one receptor type is expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator can now control the type of receptor that is utilized in a screening assay. Specific receptor sub-types and sub-subtypes can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human receptor, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value or 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes. (Danboldt et al., 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and glutaraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with the desirable properties of opioids but which lack the undesirable properties of opioids. In another embodiment, screening assays tier testing candidate substances such as agonists and antagonists of epsilon opioid receptors are used to identify such candidate substances having selective ability to interact with one or more of the opioid receptor polypeptides but which polypeptides are without a substantially overlapping activity with other opioid receptors.

Additionally, screening assays tier the testing of candidate substances are designed to allow the investigation of structure activity relationships of opioids with the epsilon receptors, e.g., study of binding of naturally occurring hormones or other substances capable of interacting or otherwise modulating with the epsilon receptor versus studies of the activity caused by the binding of such molecules to the epsilon receptor. In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced epsilon opioid receptor polypeptide in screening assays for the identification of substances which can inhibit or otherwise modify or alter the function of the receptor. The use of recombinantly produced receptor is of particular benefit because the naturally occurring receptor is present in only small quantities and has proven difficult to purify. Moreover, this provides a ready source of receptor, which has heretofore been unavailable.

As described above, receptors in the presence of agonists can exert their physiological effects through a secondary molecule. A screening assay of the invention, in preferred embodiments, conveniently employs an epsilon opioid receptor polypeptide directly from the recombinant host in which it is produced. This is achieved most preferably by simply expressing the selected polypeptide within the recombinant host, typically a eukaryotic host, followed by preparing a crude homogenate which includes the polypeptide. A portion of the crude homogenate is then admixed with an appropriate effector of the epsilon receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in *E. coli* (Berlin et al., 1992), in yeast (King et al., (1990) and in mammalian cells (Bouvier et. al. 1988).

A cell expressing a receptor can be used whole to screen agents. For example, cells expressing the receptor of the present invention can be exposed to radiolabelled agent and the amount of binding of the radiolabelled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

In that most such screening assays in accordance with the invention are designed to identify agents useful in mimicking the desirable aspects of opioids while eliminating the undesirable aspects of the hormone, preferred assays employ opioids as the normal agonist.

There are believed to be a wide variety of embodiments that can be employed to determine the effect of the candidate substance on an epsilon receptor polypeptide of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^{3}H$, $^{14}C$, $^{22}Na$, $^{32}P$, $^{35}S$, $^{45}Ca$, $^{60}Co$, $^{125}I$, and $^{131}I$. Commonly used stable isotopes include $^{2}H$, $^{13}C$, $^{15}N$, $^{18}O$.

For example, if an agent can bind to the receptor of the present invention, the binding can be detected by using radiolabelled agent or radiolabelled receptor. Briefly, if radiolabelled agent or radiolabelled receptor is utilized, the agent-receptor complex can be detected by liquid scintillation or by exposure to X-Ray film.

When an agent modifies the receptor, the modified receptor can also be detected by differences in mobility between the modified receptor and the unmodified receptor through the use of chromatography, electrophoresis or centrifugation. When the technique utilized is centrifugation, differences in mobility are known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, where an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

Where a secondary polypeptide is provided, the agent-receptor-secondary polypeptide complex or the receptor-secondary polypeptide complex can be detected. Differences in mobility or differences in spectroscopic properties as described above can be detected.

It is further contemplated that where a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Thin layer chromatographic methods (TLC), HPLC, spectrophotometric, gas chromatographic/mass spectrophotometric or NMR analyses can be used. It is contemplated that any such technique can be employed so long as it is capable of differentiating between the effector and complex, and can be used to determine enzymatic function such as by identifying or quantifying the substrate and product.

The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

A. Screening assays for epsilon opioid receptor polypeptides.

The present invention provides a process of screening a biological sample for the presence of an epsilon opioid receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the epsilon opioid receptor polypeptide whose presence is being assayed. Typically, exposure is accomplished by forming an admixture in a liquid medium that contains both the antibody and the candidate opioid receptor polypeptide. Either the antibody or the sample with the opioid receptor polypeptide can be affixed to a solid support (e.g., a column or a microliter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the opioid receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of epsilon opioid receptor polypeptide in the sample is detected by detecting the formation and presence of antibody-epsilon opioid receptor polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

B. Screening assay for anti-epsilon opioid receptor antibody.

In another aspect, the present invention provides a process of screening a biological sample for the presence of antibodies immunoreactive with an epsilon opioid receptor polypeptide (i.e., an anti-epsilon opioid receptor antibody). In accordance with such a process, a biological sample is exposed to an epsilon opioid receptor polypeptide tinder biological conditions and for a period of time sufficient for antibody-polypeptide conjugate formation and the formed conjugates are detected.

C. Screening assay for a polynucleotide that encodes an epsilon opioid receptor polypeptide.

A DNA molecule and, particularly a probe molecule, can be used for hybridizing as oligonucleotide probes to a DNA source suspected of possessing an epsilon opioid receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the opioid receptor polypeptide and account in their diversity for the redundancy inherent in the genetic code.

A suitable source of DNA for probing in this manner is capable of expressing epsilon opioid receptor polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the opioid receptor family and related polypeptides from a DNA library potentially containing such sequences; (3) primers for hybridizing to related sequences for the purpose of amplifying those sequences; (4) primers for altering the native opioid receptor DNA sequences; as well as other techniques which rely on the similarity of the DNA sequences to those of the opioid receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected opioid receptor gene. In these aspects, nucleic acid probes of an appropriate length are prepared based on a consideration of the selected opioid receptor sequence (e,g., a sequence such as that shown in SEQ ID NO: 1 or SEQ ID NO: 3. The ability of such nucleic acid probes to specifically hybridize to epsilon opioid receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the epsilon opioid receptor encoding sequence, such as that shown in SEQ ID NO: 1 or SEQ ID NO: 3. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare routants employing a mutant primer strand hybridized to an underlying template or where one seeks to isolate opioid receptor coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove non-specifically bound probe molecules, specific hybridization is detected, or even quantified, by means of the label.

D. Screening For Agonists and Antagonists

Epsilon receptors are one of the major subtypes of opioid receptors. Therefore, highly selective epsilon opioid receptor agonists are clinically usefull.

Development of highly selective, clinically useful epsilon opioid receptor agonists is facilitated by understanding the specific sites within the epsilon receptor necessary for agonist binding. The recent cloning of the epsilon opioid receptor cDNA has opened up the possibility to investigate the structural domains of this receptor subtype that are responsible for its functioning.

X. Assay kits.

In another aspect, the present invention contemplates diagnostic assay kits for detecting the presence of epsilon opioid receptor polypeptides in biological samples, where the kits comprise a first container containing a first antibody capable of immunoreacting with epsilon opioid receptor polypeptides, with the first antibody present in an amount sufficient to perform at least one assay. Preferably, assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit comprises an epsilon opioid receptor of the present invention. The kit can further contain reagents for detecting an interaction between an agent and a receptor of the present invention. The provided reagent can be radiolabelled. The kit can contain a known radiolabelled agent capable of binding or interacting with a receptor of the present invention.

It is further contemplated that the kit can contain a secondary polypeptide. The secondary polypeptide can be a G-protein. The secondary polypeptide can also be an effector protein. When a secondary polypeptide is included in a kit, reagents for detecting an interaction between the receptor and the secondary polypeptide can be provided. As a specific example, an antibody capable of detecting a receptor/G-protein complex can be provided. As another specific example, an antibody capable of detecting a G-protein/effector complex can be provided. Reagents for the detection of the effector can be provided. For example, if the effector provided is adenylyl cyclase, reagents for detecting the activity of adenylyl cyclase can be provided. The identity of such agents is within the knowledge of those skilled in the relevant art.

In an alternative aspect, the present invention provides diagnostic assay kits for detecting the presence, in biological samples, of a polynucleotide that encodes an epsilon opioid receptor polypeptides, the kits comprising a first container that contains a second polynucleotide identical or complementary to a segment of at least 10 contiguous nucleotide bases of SEQ ID NO: 1 or SEQ ID NO: 3.

In another embodiment, the present invention contemplates diagnostic assay kits for detecting the presence, in a biological sample, of antibodies immunoreactive with epsilon opioid receptor polypeptides, the kits comprising a first container containing an epsilon opioid receptor polypeptide that immunoreacts with the antibodies, with the polypeptides present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

EXAMPLES

Examples are included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

EXAMPLE 1: General Methods

A. Cloning and Amplification.

Human genomic DNA was subjected to amplification by PCR with the use of a set of degenerate primers, OR-1 and OR-2.

OR-1
5' CCTCACCA/GTGATG/CAGCG/A/TTC/GGAC/TCGA/CTA 3' (SEQ ID NO: 5),

OR-2
5' GAAGGCG/ATAG/T/CAGA/GAC/TA/G/CGGA/GTT 3' (SEQ ID NO: 6).

These degenerate oligonucleotides were derived from the compilation of sequences corresponding to the third and seventh TM regions (TM3 and TM7) of the mouse delta opioid and the related somatostatin receptors. Each primer consisted of a mixture of oligonucleotides with a number of degeneracies.

The time of PCR was 1.5 min. at 93° C., 2 min. at 55° C., and 4 min. at 72° C. (Hemmick and Bidlack, 1987). Alter 30 cycles, this DNA was phenol/chloroform extracted and ethanol precipitated. The DNA was phosphorylated with T4 polynucleotide kinase and the ends were flushed using the Klenow enzyme.

This amplified DNA was subcloned into the EcoRV site of the plasmid Bluescript as follows: the DNA was electrophoresed in soft agarose and six consecutive gel slices were cut corresponding to sizes ranging from 150 bp to 3 kb, and ligated in-gel with Bluescript (SK-) plasmid (Stratagene) overnight at room temperature. The ligation mixture of each fraction was transformed into DH5 α F' bacteria (BRL) to allow blue color selection and plated out on LB plates containing ampicillin. A human XEMBL genomic library (Clonetech) was screened using the 0.54 kb fragment of clone #12 with the same prehybridization and hybridization solutions as described below. Eighteen duplicate positive clones were picked and subsequently purified through secondary and tertiary screening. DNA was prepared frown the purified plaques, and PCR analysis identified.

This phage was cut with various enzymes to excise a probe binding insert, run on 1% agarose gel, vacuum-transferred to a nylon membrane (Gelman Sciences), UV linked and hybridized to the $6.5 \times 10^6$ cpm/ml nick-translated $^{32}$P-labeled 0.54 kb BamHI/XhoI fragment of clone #12, using the same prehybridization and hybridization solutions as below except that 1% SDS was added to decrease the background. One probe binding band, a 4.5 kb fragment, was obtained with BamHI. This 4.5 kb band was subcloned into Bluescript, and both strands of the nucleic acid sequence were determined.

B. Localization of ε mRNA.

A fragment was purified from clone #12 and radiolabeled with [α-$^{35}$S] dCTP by the random primer method to high specific activity ($10^9$ dmp/ug). Cryostate sections 8 μm in thickness were fixed in 4% paraformaldehyde in 0.1M phosphate buffer, and immersed in 15% sucrose in 0.1M phosphate buffer. Sections were rinsed in 2×SSC for 10 minutes and permeabilized in the same buffer containing 0.5% Trition X-100 for 15 minutes, rinsed twice in 2×SSC and prehybridized for 1 hour at 42° C. in the following buffer: 5×SSC containing 5× Denhardt's solution (0.2% Ficoll/0.2% bovine serum albumin/0.02% polyvinylpryrrolidine), 200 μg yeast tRNA/ml, 200 μg denatured salmon sperm DNA/ml, and 50% formamide.

Hybridization was carried out for 24 hours at 42° C. in the prehybridization buffer containing 4% dextran sulphate and $10^6$ cpm heat-denatured $^{35}$S-labelled clone #12 per section. Following hybridization, the slides were washed at room temperature in 2×SSC for 2 hours, 1×SSC for 1 hours, 0.5×SSC for 1 hour and at 42° C. in 0.5×SSC for 1 hour. The slides were dehydrated in ethanol and air dried. Autoradiographic detection of hybrids was carried out using an X-ray autoradiogram and by dipping the slide in Kodak NTB2 emulsion diluted 1:1 with distilled water. They were air dried for 1 hour and placed in 4° C. desiccated chamber for 7 days. They were subsequently developed for 4 minutes in Kodak D-19 developer, washed in water for 1 minute, and fixed for 5 minutes in Kodak Fixer. Alter washing for 1 hours, they were stained with hematoxylin and cosin (H and E) and coverslipped. Controls consisted of prior digestion of pituitary tissues with 300 μg/ml of RNase (Sigma) at 37° C. for 45 minutes. RNAse controls were run on all samples.

C. Fluorescence in situ hybridization.

Probes were biotinylated with dATP using the BRL Bionick labelling kit. In situ hybridization and FISH detection: lymphocytes were cultured in a minimal essential medium (MEM) supplemented with 10% fetal calf serum and phytohemagglutinin (PHA) at 37° C. for 68–72 hr. The lymphocyte cultures were treated with BrdU (18 mg/ml Sigma) for an additional 16 hr to synchronize the cell population. The synchronized cells were washed three time with serum free medium and incubated at 37° C. for 6 hours in α-MEM with thymidine (2.5 ug/ml: Sigma). Cells were harvested and slides were made by busing procedures. The procedure for fluorescence in situ hybridization (FISH) was performed according to Heng et al, 1992 and Heng and Tsui 1993. Briefly slides aged 7 days were baked 55° C. for 1 hour. After RNase A treatment, the slides were denatured in 70% formamide in 2×SSC for 1 minute at 70° C. followed by dehydration with ethanol. The probe was denatured at 75° C. for 5 minutes in a hybridization mix consisting of 50% formamide and 10% dextran sulphate. After hybridization, detection and amplification, the FISH signals and the DAPI banding pattern was visualized in one single operation by simply switching the filters of the microscope (Heng and Tsui 1993).

EXAMPLE 2: Isolation of cDNA clones

Several of the rodent opioid receptors (OR) have now been cloned, the δ, κ, and μ (Yasuda et al., 1993 and Chen et al., 1993). Two degenerate oligonucleotides based on the nucleotide sequence encoding the third and seventh transmembrane (TM) regions of the mouse δ opioid receptor were prepared. Because many previously clone G protein-coupled receptors are encoded on single exons, those oligonucleotides were used to amplify in the polymerase chain reaction (PCR) human genomic DNA (Hazum et al., 1979). The amplified DNA (in the size range 500 to 1000 bp) was subcloned into the Bluescript plasmid, and 150 of the resulting clones were sequenced.

From the nucleotide sequences obtained it appeared that none of the genomic PCR clones encoded the human orthologues of the rodent OR. Two clones, #11 and #12, shared identity with the δ, μ and κ ORs. To obtain the full length gene encoded by those PCR-derived fragments (540 bp), a human genomic library was screened and 18 positive clones were obtained from the screening. Rapid PCR analysis of these phage clones with the original PCR oligonucleotides succeeded in identifying one phage each, which contained the sequence of clone #11 or #12. These phages were purified and a fragment (4.5 kb) from clones #11 and #12 was subcloned into the Bluescript plasmid and sequenced.

These genomic clones, named HG-11 and HG-12, contained intronless reading frames of about 980 to about 1000 nucleotides, encoding a 333 or 327 amino acid protein (see FIGS. 1A–1C and FIGS. 2A–2D). PCR analysis using two oligonucleotides specific for clone #12 sequence identified identically sized DNA fragments in chimpanzee, monkey, rat and mouse genomic DNA.

EXAMPLE 3: Pharmacology of Epsilon Receptor Polypeptide

To establish that HG-12 encoded an opioid receptor, a 2 kb fragment was removed from the 5' untranslated region of the gene and the shortened insert (2.5 kb) was subcloned into the multiple cloning site of the eukaryotic expression vector (pRC/CMV). The ability of selective opioid receptor agonists and antagonists to bind the membranes of transfected COS and BHK cells was assessed. Cells transfected with this construct bound [$^3$H]bremazocine, a benzoinorphan ligand with high affinity for all known opioid receptor subtypes, with a $K_d$ of 10 nM. Specific [$^3$H]bremazocine binding was defined in the presence of the opiate alkaloid levorphanol, and was effectively displaced by δ-funaltrexamine with an $IC_{50}$ 100 nM and by $IC_{50}$ 1000 nM, as shown in FIGS. 3A–3C and FIG. 4. Membranes prepared from control untransfected cells did not display displaceable [$^3$H]bremazocine binding. [$^3$H]bremazocine binding was displaced by (Leu$^5$) δ-endorphin, and to a lesser extent by DADLE, but not by the ligands selective for μ, δ or κ opioid receptors, DAMGO, DPDPE and U-50,488.

EXAMPLE 4: Southern and Northern Blot Analysis

Figure 5:
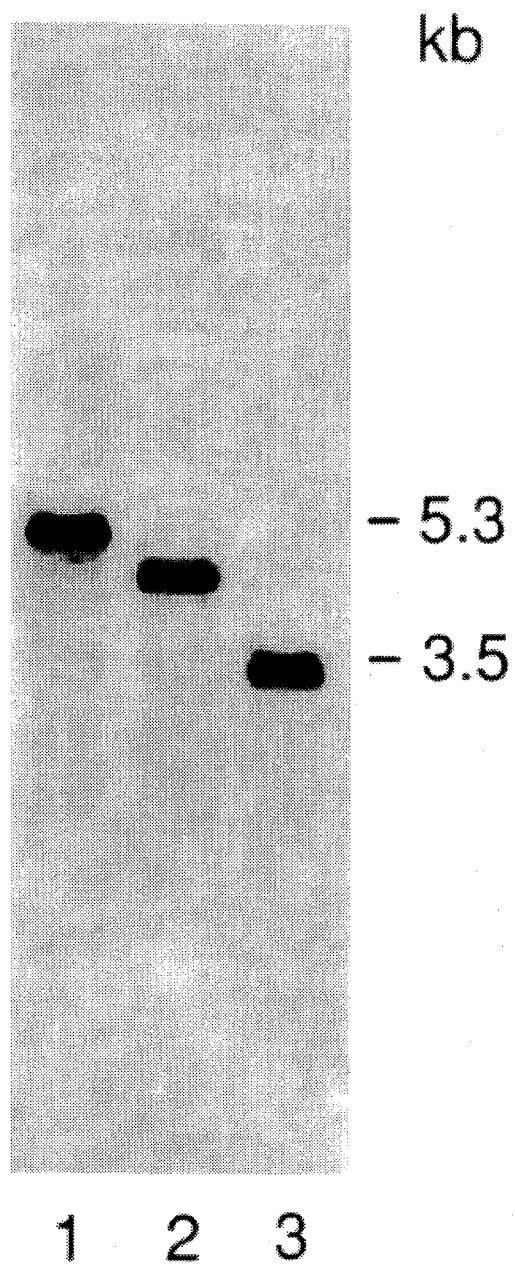
FIG. 5 shows a Southern blot analysis of human DNA. Human genomic DNA was digest with HindIII, PstI, and SacI, subjected to electrophoresis (1%) agarose gel, and Southern-blot hybridization with DNA probe clone #12. Human DNA was isolated from blood samples.
Figure 6:
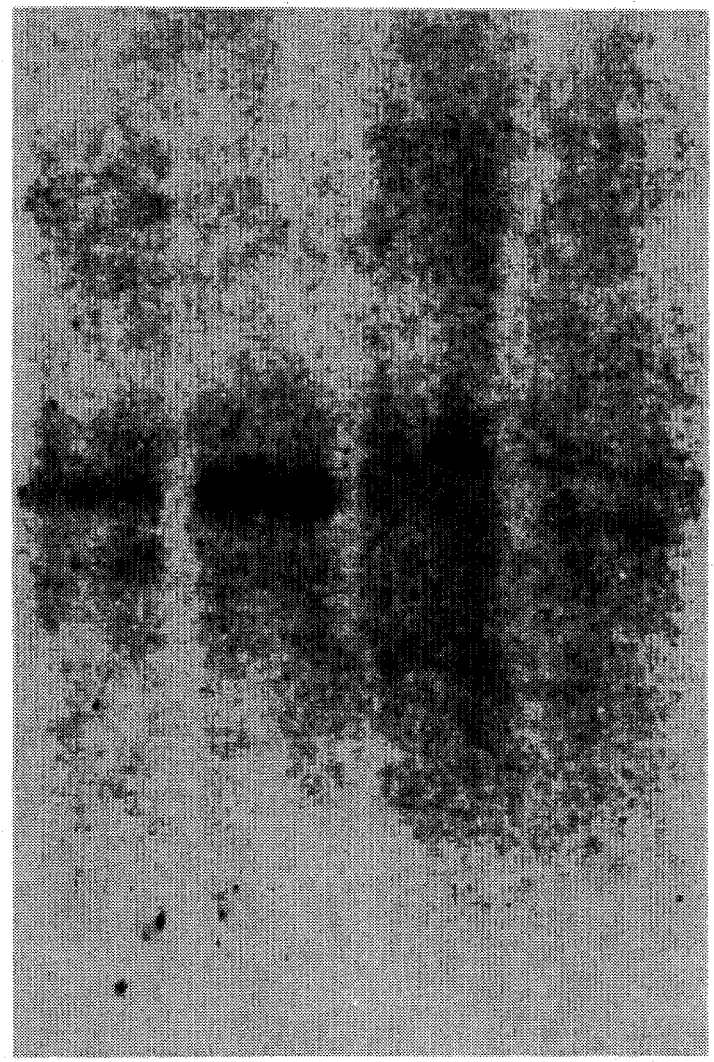
FIG. 6 shows a Northern blot analysis of selected human and rodent tissues. Human and rat mRNAs from striatum, pituitary, hypothalamus, frontal cortex and cerebellum were extracted, run on formaldehyde agarose gel and blotted on nylon. The blots were then probed with the P-labeled fragment, washed with 2×SSC, 0.1% SDS at 50° C. for 20 minutes and with 0.1×SSC, 0.1% SDS and exposed to X-ray film overnight at −70° with intensifying screen.

When human genomic DNA was digested with various restriction enzymes and subjected to Southern hybridization analysis with a DNA probe isolated from the coding region of HG-12, only a single hybridizing band was observed with each enzyme. HG-12 did not cross hybridize with other related genes and the single hybridizing band observed was consistent with an intronless gene structure. Northern blot analysis of several human brain regions and tissues revealed a single mRNA transcript in the cerebellum and frontal cortex, while two transcripts were visible in the pituitary and hypothalamus. No specific mRNA was detected in kidney, and liver. In, situ hybridization histochemistry in pituitary revealed a strong signal showing restricted distribution of HG-12 in a subpopulation of cells. The signal distribution was preferentially localized in the lateral wings of the gland with the central portion and the posterior pituitary being devoid of labelling. Data from the Southern and Northern blots are shown in FIGS. 5 and 6, respectively.

EXAMPLE 5: Fluorescence in situ Hybridization.

Figure 7:
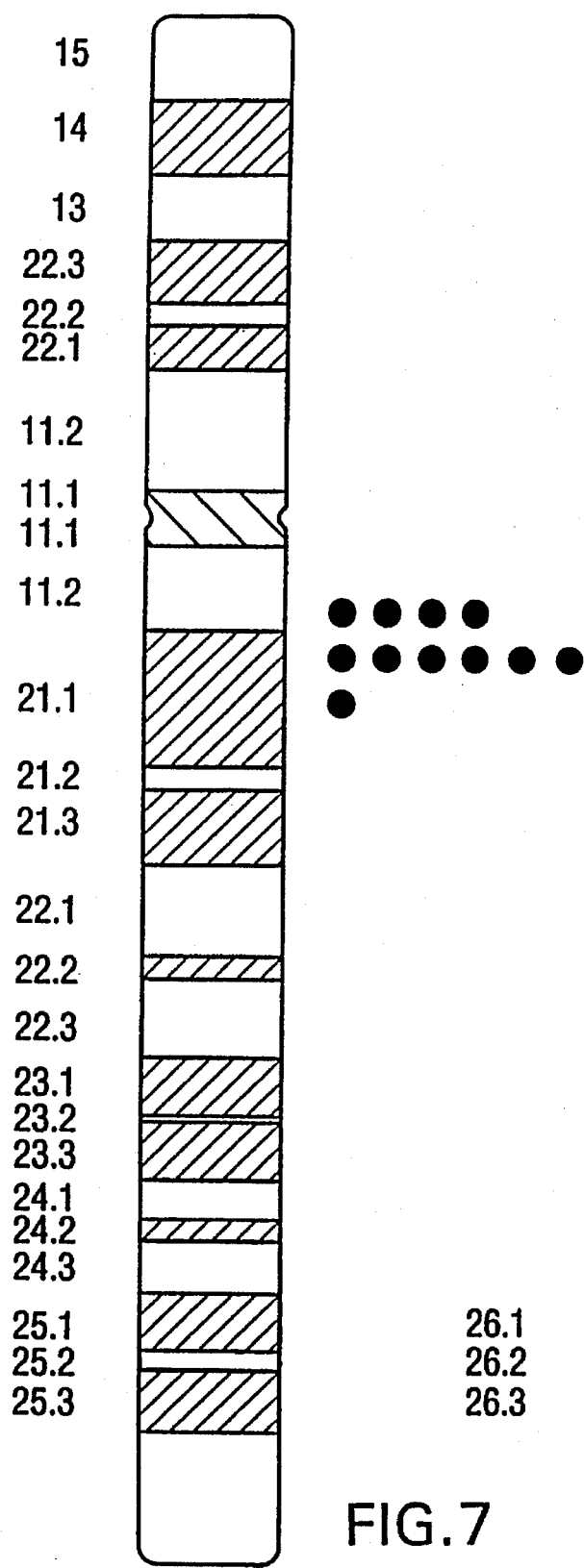
FIG. 7 shows a summary of FISH data for human clone 12 on chromosome 10. Each dot represents a double fluorescent signal on DAPI-banded chromosomes.

Fluorescence in situ hybridization (FISH)[9] was used to identify the specific chromosomal localization of HG-12 gene. Sixty mitotic chromosome structures were examined and 42 of them (70%) showed double hybridization signals on banded chromosome 10, one on each of the two sister chromatids. A total of 11 mitotic figures were photographed and the data are summarized in FIG. 7. Various degrees of condensed chromosomes were used for detailed localization, and all of the signals scored were located within the bands of 10 q11.2 to 10 q21.1 (FIG. 7). There was no cross hybridization from other loci of the human genome under the FISH detection conditions used.

The opioid receptor we have cloned has a structure typical of the G protein-coupled receptors, and interacts specifically with the 6,7-benzomorphan drugs and the endogenous peptide δ-endorphin, but not with the selective μ, δ and κ opioid ligands. Collectively, these data provide direct evidence for the cloning and identification of the ε opioid receptor from human brain.

REFERENCES CITED

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Akil, H. et al. (1984) *Annu. Rev. Neurosci.* 7:223.
Attali, B. et al. (1989) *J. Neurochem.* 52:360.
Berg J. M. (1988) *Proc. Natl. Acad. Sci. U.S.A.* 85:99–102.
Bertin, B. et al. (1992) *J. Biol. Chem.* 267(12):8200.
Bero et al. (1988) *Mol. Pharmacol.* 34:614.
Bertolucci, M. et al. *Neurosci. Abstr.* 18L1368.
Bolivar et al. (1977) *Gene,* 2:95.
Boshart et al. (1985) *Cell* 41:521.
Bouvier, M. et al. (1988) *Mol. Pharmacol.* 33:133.
Bradbury, A. F. et al. (1976) *Nature* 260:165.
Breder, C. D. et al. (1992) *J. Neurosci,* 12:3920.
Butt et al. (1990) *Biophys. J.* 58:1473.
Chang et al. (1978) *Nature,* 375:615.
Chen et al. (1993) *Mol. Pharmacol.* 44:8.
Chomczynski, P. and Sacchi, N. (1987) *Ana Biochem.* 162:156.
Clark, J. A. et al. (1989) *J. Pharmacol. Exp. Therapeut.* 251:461.
Corbett et al. (1993) *Handb. Exp. Pharmacol. Sci.* 8:456.
Cotecchia et al. (1988) *Proc. Natl. Acad. Sci. USA* 85:7159.
Cotecchia et al. (1990) *Proc. Natl. Acad. Sci. USA* 87:2896.
Crea et al. (1978) *Proc. Natl. Acad. Sci. U.S.A.,* 75:5765.
Danboldt, N. C. et al. (1990) *Biochemistry* 29(28):6734.
Di Chiara, G. et al. (1992) *Trends Pharmacol. Sci.* 13:185.
Dohlman (1987) *Biochemistry* 26:2657.
Dohlman, H. G. (1991) *Annu. Rev. Biochem,* 60:166–170; 174–s176; 653–688.
Drake et al. (1989) *Science* 243: 1586.
Durbin, S. D. and W. E. Carlson (1992) *J. Crystal Growth* 122:71.
Edstrom et al. (1990) *Biophys. J.* 58:1437.
Evans et al. (1992) *Science* 258:1952.
Evans, R. M. and S. M. Hollenberg (1988) *Cell* 52:1–3.
Ferruti, P. and M. C. Tanzi, (1986) *Cris. Rev. Ther. Drug Carrier Syst.* 2:117.
Fiers et al. (1978) *Nature* 273:113.
Frielle, T. et al. (1988) *Proc. Natl. Acad. Sci. USA* 85:9484.
Gabizon, A. et al. (1990) *Cancer Res.* 50:6371–6378
Gilman et al. (1982) *Proc. Natl./Acad. Sci. USA* 79:4226.
Gilmore, W. and Weiner L. P. (1988) *J. Neuroimmunol.* 18:125.
Gioannini, T. L. et al. (1989) *J. Mol. Recogn.* 2:44.
Goeddel et al. (1979) *Nature,* 281:544.
Goeddel et al. (1980) *Nucleic Acids Res.,* 8:4057.
Gransch, C. et al. (1988) *J. Biol. Chem.* 263:5853.
Hansma et al. (1992) *Science* 256:1180.
Harlow, E. and D. Lane (1988) *Antibodies: "A Laboratory Manual,"* Cold Spring Harbor Laboratory.
Hazum et al. (1979) *Science* 205:1033.
Hemmick, L M and Bidlack J M (1987) *Life Sci.* 41:1971.
Henderson et al. (1992) *Science* 257:1944.
Heng et al. (1992) *Proc. Natl. Acad. Sci. USA* 89:9509.
Heng, H. and Tsui, L. C. (1993) *Chromosoma* 102:325
Hess et al. (1968) *J. Adv. Enzyme Reg.* 7:149.
Hitzeman et al. (1980) *J. Biol. Chem.* 255:2073.
Hoh et al (1991) *Science* 253:1405.

Holland et al. (1978) *Biochemistry* 17:4900.
Horstman, D. A. et al. (1990) *J. Biol. Chem.*, 265:21590.
Hsia, J. A. et al. (1984) *J. Biol. Chem,.* 259:1086.
Hughes, J. et al. (1975) *Nature* 258:577.
Itakura et al. (1977) *Science* 198:1056.
Johnson et al. (1990) *Mol. Pharm.* 38:289.
Jones (1977) *Genetics* 85:12.
Kanaho et al. (1984) *J. Biol. Chem.* 259:7378.
Kennelly, P. J. et al. (1991) *J. Biol. Chem,.* 266:15555.
King et al. (1990) *Science* 250:121.
Kingsman et al. (1979) *Gene* 7:141.
Klug, A. and D. Rhodes (1987) *Trends Biochem. Sci.* 12:464–469.
Kobilka, B. K. et al. (1987) *J. Biol. Chem.* 262:7321.
Kobilka, B. K. et al. (1988) *Science* 240:1310.
Koob, G. F. et al. (1992) *Trends Neurosci.* 15:186.
Kozasa et al. (1988) *Proc. Natl. Acad. Sci USA* 85:2081.
Kruse and Patterson, eds. (1973) *Tissue Culture*, Academic Press.
Kyte, J., and R. F. Doolittle (1982) *J. Mol. Biol.* 157:105.
Lal et al. (1993) *Am. J. Physiol.* in press.
Lal, R. and L. Yu (1993) *Proc. Natl. Acad. Sci. USA*, 90:7280.
Loh, H. H. et al. (1990) *Annu. Rev. Pharmacol. Toxicol.* 30:123.
Lomasney et al. (1990) *Proc. Natl. Acad. Sci. USA* 87:5094.
Lutz, R. A. et al. (1992) *J. Receptor Res.* 12:267.
Mandler et al. (1986) *J. Immuno.* 136:934.
Mansour, A. et al. (1987) *J. Neurosci.* 7:2445.
Marullo et al. (1988) *Proc. Natl. Acad. Sci. USA* 85:7551.
Mathews et al. (1983) *J. Immunol.* 130:1658.
Messing et al., *Third Cleveland Symposium on Macromolecules and Recombinant DNA*, Editor A. Walton, Elsevier, Amsterdam (1981).
Miller, J. et al. (1985) *EMBO J.* 4:1609–1614.
Nathans et al. (1986 A) *Science* 232:193.
Nathans et al. (1986 B) *Science* 232:203
Nock, B. et al. (1988) *Eur. J. Pharmacol.* 154:27.
Ngeyen et al. (1991a) *Gene* 109:211.
Okayarea et al. (1983) *Mol. Cell Biol.* 3:280.
Olson, G. A. et al. (1989) *Peptides* 10:1253.
Ott, S. et al. (1988) *J. Biol. Chem.* 263:10524.
Parker, E. and E. M. Ross (1991) *J. of Biol. Chem.* 266:15.
Payette et al. (1990) *FEBS Lett.* 266:21.
Payre, F. and A. Vincent (1988) *FEBS Lett.* 234:245–250.
Pert, C. G. et al. (1973) *Science* 179:1011.
Pert, C. B. et al. (1974) *Mol. Pharmacol.* 10:868.
Pfeiffer, A. et al. (1986) *Science* 223:774.
Puppo et al. (1985) *Immunopharmacology* 10:119.
Puttfarcken, P. S. et al. (1988) *Mol. Phannacol.* 33:520.
Ranade, V. V. (1989) *J. Clin. Pharmacol.* 29:685–694
Regan et al. (1988) *Proc. Natl. Acad. Sci. USA* 85:6301.
Sacerdote, p. and Panerai, AE *Peptides* 10:565.
Sambrook, J. et al. (1989) *Molecular Cloning: A Laboratory Manual* (Cold Spring Harbor Laboratory Press, Cold Spring Harbor, N.Y.).
Schweigerer et al. (1985) *Proc. Natl. Acad. Sci. USA* 82:5751.
Seeburg (1982) *DNA* 1:239.
Shahabi et al. (1990) *Endocrinology* 126:3006.
Singhal et al. (1992) *Nephron* 62:66.
Shook, J. E. et al. (1990) *Am. Rev. Respir. Dis.* 142:895.
Siebwenlist et al. (1980) *Cell*, 20:269.
Simon, E. J. (1991) *Medicinal Res. Rev.* 11:357.
Stinchcomb et al. (1979) *Nature*, 282:39.
Strattbrd-Perricaudet et al. (1992).
Strotchman and Simon (1991).
Suryanarayama et al. (1992) *J. Biol. Chem.* 267:21991.
Thomsen et al. (1984) *PNAS* 81:659.
Tschemper et al. (1980) *Gene* 10:157.
Unterwald, E. M. et al. (1991) *Brain Res.* 562:57.
Unterwald, E. M. et al. (1987) *Eur. J. Pharmacol.* 133:275.
Van Epps, D. E. and Saland, L. (1984) *J. Immunol.* 132:3046.
Weisenhorn et al. (1990) *Biophys. J.* 58:1251.
Xie, G-X. et al. (1992) *Proc. Natl. Acad. Sci. USA* 89:4124.
Yamada, Y. et al. (1992) *Proc. Natl. Acad. Sci. USA* 89:251.
Yasuda, K. et al. (1992) *J. Biol Chem.* 267:20422.
Yasuda et al. (1993) *Proc. Natl. Acad. Sci. USA* 90:6736.
Yokota, Y. et al. (1992) *EMBO J.* 11:3585.
Zukin, R. S. et al. (1988) *Proc. Natl. Acad. Sci. USA* 85:4061.

---

What is claimed is:

1. An isolated and purified polynucleotide that encodes an opioid receptor polypeptide comprising the amino acid residue sequence of SEQ ID NO: 2.

2. The isolated and purified polynucleotide of claim 1, wherein said polynucleotide is a DNA molecule.

3. The DNA molecule of claim 2, wherein said encoded polypeptide comprises the amino acid residue sequence of SEQ ID NO: 2.

4. The isolated and purified polynucleotide of claim 1, wherein said polynucleotide comprises the nucleotide base sequence of SEQ ID NO: 1.

5. An isolated and purified polynucleotide comprising a base sequence that is identical or complementary to a segment of more than 25 contiguous bases of SEQ ID NO: 1, wherein said polynucleotide hybridizes under a hybridization condition employing between 0.02 to 0.15 NaCl and 50° C. to 70° C. temperature to a polynucleotide that encodes an opioid receptor polypeptide comprising the amino acid residue sequence of SEQ ID NO: 2 or its complementary sequence.

6. The isolated and purified polynucleotide of claim 5, wherein the polynucleotide comprises a base sequence that is identical or complementary to a segment of 40 contiguous bases of SEQ ID NO: 1 and wherein said polynucleotide hybridizes under a hybridization condition employing between 0.02 to 0.15 NaCl and 50° C. to 70° C. temperature to a polynucleotide that encodes an opioid receptor polypeptide comprising the amine acid residue sequence of SEQ NO: 2 or its complementary sequence.

7. The isolated and purified polynucleotide of claim 5, wherein the polynucleotide comprises a base sequence that is identical or complementary to a segment of 55 contiguous bases of SEQ ID NO: 1 and wherein said polynucleotide hybridizes under a hybridization condition employing between 0.02 to 0.15 NaCl and 50° C. to 70° C. temperature to a polynucleotide that encodes an opioid receptor polypeptide comprising the amine acid residue sequence of SEQ ID NO: 2 or its complementary sequence.

8. The isolated and purified polynucleotide of claim 5, wherein the polynucleotide comprises a base sequence that is identical or complementary to a segment of 70 contiguous bases of SEQ ID NO: 1 and wherein said polynucleotide hybridizes under a hybridization condition employing between 0.02 to 0.15 NaCl and 50° C. to 70° C. temperature to a polynucleotide that encodes an opioid receptor polypeptide comprising the amine acid residue sequence of SEQ ID NO: 2 or its complimentary sequence.

9. An expression vector comprising a polynucleotide that encodes an opioid receptor polypeptide comprising the amine acid residue sequence of SEQ ID NO: 2.

10. The expression vector of claim 9, wherein the polynucleotide comprises the nucleotide base sequence of SEQ ID NO: 1.

11. A recombinant host cell transfected with a polynucleotide that encodes an opioid receptor polypeptide comprising the amino acid residue sequence of SEQ ID NO: 2.

12. The recombinant host cell of claim 11, wherein the polynucleotide comprises the nucleotide sequence of SEQ ID NO: 1.

13. A process of preparing an opioid receptor polypeptide comprising:

(a) transfecting a cell with a polynucleotide that encodes a polypeptide comprising the amino acid residue sequence of SEQ ID NO: 2 to produce a transformed host cell; and (b) maintaining the transformed host cell under biological conditions sufficient for expression of the polypeptide.

14. The method of claim 13, wherein the polynucleotide comprises the nucleotide base sequence of SEQ ID NO: 1.

* * * * *